(12) United States Patent
Cote et al.

(10) Patent No.: US 8,735,554 B2
(45) Date of Patent: May 27, 2014

(54) **REAGENTS, METHODS, AND SYSTEMS FOR DETECTING METHICILLIN-RESISTANT *STAPHYLOCOCCUS***

(75) Inventors: Colette Cote, Germantown, MD (US); Qiao-xi Zheng, Hanover, MD (US); Venkatakrishna Shyamala, N. Potomac, MD (US); Tom Hazel, San Jose, CA (US)

(73) Assignee: Innovative Biosensors, Inc., Rockville, MD (US)

( * ) Notice: Subject to any disclaimer, the term of this patent is extended or adjusted under 35 U.S.C. 154(b) by 338 days.

(21) Appl. No.: 12/991,679

(22) PCT Filed: May 7, 2009

(86) PCT No.: PCT/US2009/043143
§ 371 (c)(1),
(2), (4) Date: Jun. 14, 2011

(87) PCT Pub. No.: WO2009/137677
PCT Pub. Date: Nov. 12, 2009

(65) Prior Publication Data
US 2011/0250202 A1    Oct. 13, 2011

Related U.S. Application Data

(60) Provisional application No. 61/126,831, filed on May 7, 2008, provisional application No. 61/092,267, filed on Aug. 27, 2008.

(51) Int. Cl.
*C07K 16/12* (2006.01)
*G01N 33/569* (2006.01)

(52) U.S. Cl.
USPC .................................... 530/388.4; 435/7.32

(58) Field of Classification Search
None
See application file for complete search history.

(56) References Cited

U.S. PATENT DOCUMENTS

| | | |
|---|---|---|
| 2003/0187225 A1 | 10/2003 | Penichet et al. |
| 2003/0224000 A1 | 12/2003 | Kokai-Kun et al. |
| 2005/0226883 A1 | 10/2005 | Averback et al. |
| 2006/0073151 A1 | 4/2006 | Jay et al. |
| 2007/0037163 A1 | 2/2007 | Doucette-Stamm et al. |

FOREIGN PATENT DOCUMENTS

WO    WO 00/71585    11/2000

OTHER PUBLICATIONS

International Search Report, PCT/US2009 /043143, Oct. 13, 2009.
International Preliminary Report on Patentability (IPRP), PCT/US2009 /043143, Oct. 13, 2009.
Written Opinion of the International Searching Authority, PCT/US2009 /043143, Oct. 13, 2009.
European Extended Search Report dated Apr. 6, 2011, from related EP Appl. No. 09743663.8, 7 pages.
Saito et al., "Immunological detection of penicillin-binding protein 2' of methicillin-resistant staphylococci by using monoclonal antibodies prepared from synthetic peptides", Journal of Clinical Microbiology, vol. 33, No. 9, 1995, pp. 2498-2500.
Udo et al., "Rapid detection of methicillin resistance in staphylococci using a slide latex agglutination kit", International Journal of Antimicrobial Agents, Elsevier Science, Amsterdam, NL, vol. 15, No. 1, Jun. 1, 2000, pp. 19-24.
Sekiguchi et al., "Detection of methicillin-resistant *Staphylococcus aureus* (MRSA) with antibodies against synthetic peptides derived from penicillin-binding protein 2'", Microbiology and Immunology, Center For Academic Publications Japan, vol. 39, No. 8, Jan. 1, 1995, pp. 545-550.
Ohara et al., "Immunological detection of penicillin-binding protein 2' in clinical isolates of methicillin-resistant *Staphylococcus aureus* and *Staphylococcus epidermidis*", FEMS Microbiology Letters, Blackwell Publishing, Amsterdam, NL, vol. 57, No. 1, Jan. 1, 1989, pp. 97-104.
Knausz et al., "Rapid detection of methicillin resistance in teicoplanin-resistant coagulase-negative staphylococci by a penicillin-binding protein 2' latex agglutination method", Journal of Microbiological Methods, Elsevier, Amsterdam, NL, vol. 60, No. 3, Mar. 1, 2005, pp. 413-416.
Hussain et al., "Rapid detection of mecA-positive and mecA-negative coagulase-negative staphylococci by an anti-penicillin binding protein 2a slide latex agglutination test", Journal of Clinical Microbiology, vol. 38, No. 6, Jun. 2000, pp. 2051-2054.
Horstkotte et al., "Rapid detection of methicillin resistance in coagulase-negative staphylococci by a penicillin-binding protein 2a-specific latex agglutination test", Journal of Clinical Microbiology, vol. 39, No. 10, Oct. 2001, pp. 3700-3702.

*Primary Examiner* — Brian J Gangle
(74) *Attorney, Agent, or Firm* — Cooley LLP

(57) ABSTRACT

The present invention provides PBP2a peptide antigens for generating antibodies against MRSA, and provides high-affinity binding agents that detect MRSA by selective immunoreactivity with PBP2a. The antibodies are useful in methods and systems for detecting MRSA, including biosensor systems, or as components of diagnostic or detection kits. The antibodies, in some embodiments, have therapeutic value against MRSA infection.

35 Claims, 6 Drawing Sheets

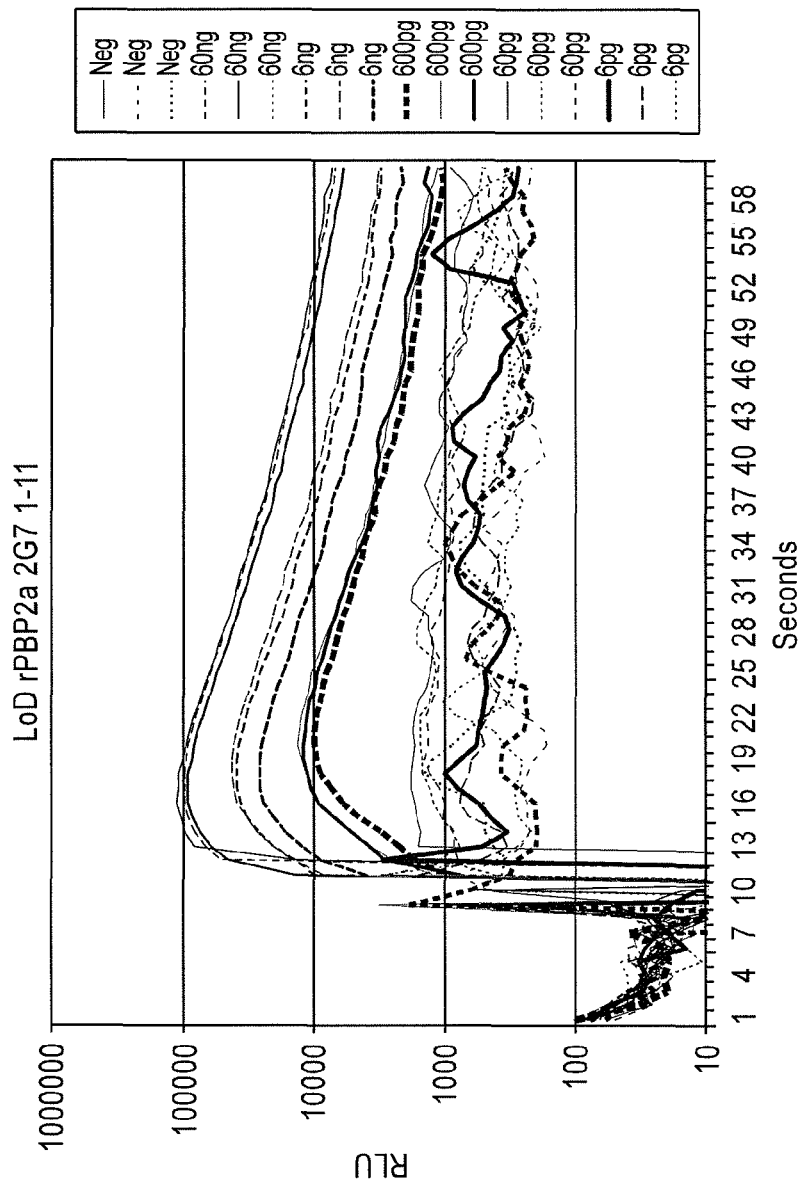

SEQUENCE LISTING

```
<160> NUMBER OF SEQ ID NOS: 13

<210> SEQ ID NO 1
<211> LENGTH: 15
<212> TYPE: PRT
<213> ORGANISM: Staphylococcus aureus

<400> SEQUENCE: 1

Asp Lys Glu Ile Asn Asn Thr Ile Asp Ala Ile Glu Asp Lys Asn
1               5                   10                  15

<210> SEQ ID NO 2
<211> LENGTH: 108
<212> TYPE: PRT
<213> ORGANISM: Mus sp.

<400> SEQUENCE: 2

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Ser Ile Gly Thr Ser
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Ser Asn Arg Trp Pro Phe
```

```
                        85                  90                  95
Thr Phe Gly Ser Gly Thr Lys Leu Glu Ile Lys Arg
                100                 105

<210> SEQ ID NO 3
<211> LENGTH: 120
<212> TYPE: PRT
<213> ORGANISM: Mus sp.

<400> SEQUENCE: 3

Glu Val Gln Leu Gln Gln Ser Gly Ala Glu Phe Val Lys Arg Pro Gly
1               5                   10                  15

Ala Ser Val Lys Leu Ser Cys Arg Val Ser Gly Phe Asn Ile Lys Asp
            20                  25                  30

Tyr Tyr Ile Asn Trp Val Lys Gln Arg Thr Glu Gln Gly Leu Glu Trp
        35                  40                  45

Ile Gly Arg Ile Asp Pro Glu Asp Gly Glu Thr Lys Tyr Ala Pro Lys
    50                  55                  60

Phe Gln Gly Lys Ala Thr Ile Thr Ala Asp Thr Ser Ser Asn Thr Ala
65                  70                  75                  80

Asn Leu His Leu Ser Ser Leu Thr Ser Ala Asp Thr Ala Val Tyr Tyr
                85                  90                  95

Cys Ala Ser Ser Gly Tyr Ala Phe Ala Trp Phe Leu Tyr Trp Gly Gln
                100                 105                 110

Gly Thr Leu Val Thr Val Ser Ala
        115                 120

<210> SEQ ID NO 4
<211> LENGTH: 107
<212> TYPE: PRT
<213> ORGANISM: Mus sp.

<400> SEQUENCE: 4

Gln Asn Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys Arg
                100                 105

<210> SEQ ID NO 5
<211> LENGTH: 117
<212> TYPE: PRT
<213> ORGANISM: Mus sp.

<400> SEQUENCE: 5

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Tyr
            20                  25                  30
```

```
Phe Ile His Trp Val Asn Gln Arg Thr Lys Gln Gly Leu Glu Trp Ile
            35                  40                  45

Gly Arg Ile Asp Pro Glu Asp Gly Glu Thr Lys Tyr Ala Pro Lys Phe
 50                  55                  60

Gln Gly Lys Ala Thr Leu Thr Ala Asp Thr Thr Ser Asn Thr Ala Asp
 65                  70                  75                  80

Leu Gln Leu Ser Ser Leu Thr Ser Glu Asp Thr Ala Val Tyr Tyr Cys
                 85                  90                  95

Val Leu Tyr Tyr Ser Arg Ser Phe Asp Tyr Trp Gly Gln Gly Thr Thr
            100                 105                 110

Leu Thr Val Ser Ser
        115
```

<210> SEQ ID NO 6
<211> LENGTH: 108
<212> TYPE: PRT
<213> ORGANISM: Mus sp.

<400> SEQUENCE: 6

```
Asp Ile Leu Leu Thr Gln Ser Pro Ala Ile Leu Ser Val Ser Pro Gly
 1               5                  10                  15

Glu Arg Val Ser Phe Ser Cys Arg Ala Ser Gln Ser Ile Gly Thr Ser
             20                  25                  30

Ile His Trp Tyr Gln Gln Arg Thr Asn Gly Ser Pro Arg Leu Leu Ile
         35                  40                  45

Lys Tyr Ala Ser Glu Ser Ile Ser Gly Ile Pro Ser Arg Phe Ser Gly
 50                  55                  60

Ser Gly Ser Gly Thr Asp Phe Thr Leu Ser Ile Asn Ser Val Glu Ser
 65                  70                  75                  80

Glu Asp Ile Ala Asp Tyr Tyr Cys Gln Gln Ser Asn Arg Trp Pro Phe
                 85                  90                  95

Thr Phe Gly Ser Gly Thr Lys Leu Glu Ile Lys Arg
            100                 105
```

<210> SEQ ID NO 7
<211> LENGTH: 119
<212> TYPE: PRT
<213> ORGANISM: Mus sp.

<400> SEQUENCE: 7

```
Glu Val Gln Leu Gln Gln Ser Gly Ala Glu Phe Val Lys Pro Gly Ala
 1               5                  10                  15

Ser Val Lys Leu Ser Cys Arg Val Ser Gly Phe Asn Ile Lys Asp Tyr
             20                  25                  30

Tyr Ile Asn Trp Val Lys Gln Arg Thr Glu Gln Gly Leu Glu Trp Ile
         35                  40                  45

Gly Arg Ile Asp Pro Glu Asp Gly Glu Thr Lys Tyr Ala Pro Lys Phe
 50                  55                  60

Gln Gly Lys Ala Thr Ile Thr Ala Asp Thr Ser Ser Asn Thr Ala Asn
 65                  70                  75                  80

Leu His Leu Ser Ser Leu Thr Ser Ala Asp Thr Ala Val Tyr Tyr Cys
                 85                  90                  95

Ala Ser Ser Gly Tyr Ala Phe Ala Trp Phe Tyr Trp Gly Gln Gly
            100                 105                 110

Thr Leu Val Thr Val Ser Ala
        115
```

<210> SEQ ID NO 8
<211> LENGTH: 324
<212> TYPE: DNA
<213> ORGANISM: Mus sp.

<400> SEQUENCE: 8

| | | | | |
|---|---|---|---|---|
| gacatcttgc tgactcagtc tccagccatc ctgtctgtga gtccaggaga aagagtcagt | | | | 60 |
| ttctcctgca gggccagtca gagcattggc acaagcatac actggtatca gcaaagaaca | | | | 120 |
| aatggttctc caaggcttct cataaagtat gcttctgagt ctatctctgg gatcccttcc | | | | 180 |
| aggtttagtg gcagtggatc agggacagat tttactctta gcatcaatag tgtggagtct | | | | 240 |
| gaagatattg cagattatta ctgtcaacaa agtaatagat ggccattcac gttcggctcg | | | | 300 |
| gggacaaagt tggaaataaa acgg | | | | 324 |

<210> SEQ ID NO 9
<211> LENGTH: 358
<212> TYPE: DNA
<213> ORGANISM: Mus sp.

<400> SEQUENCE: 9

| | | | | |
|---|---|---|---|---|
| gaggttcagc tgcagcagtc tggggcagag tttgtgagag ccaggggcct cagtcaagtt | | | | 60 |
| gtcctgcaga gtttctggct tcaacattaa ggactactat attaactggg tgaagcagag | | | | 120 |
| gactgaacag ggcctggagt ggattggaag gattgatcct gaggatggtg aaactaaata | | | | 180 |
| tgccccgaaa ttccagggca aggccactat aacagcagac acatcctcca cacagccaa | | | | 240 |
| cctgcacctc agcagcctga catctgcgga cactgccgtc tattactgtg ctagctcagg | | | | 300 |
| ctacgccttt gcctggtttc tttactgggg tcagggact ctggtcactg tctctgca | | | | 358 |

<210> SEQ ID NO 10
<211> LENGTH: 321
<212> TYPE: DNA
<213> ORGANISM: Mus sp.

<400> SEQUENCE: 10

| | | | | |
|---|---|---|---|---|
| caaaatgttc tcacccagtc tccagcaatc atgtctgcat ctccagggga gaaggtcacc | | | | 60 |
| atgacctgca gtgccagctc aagtgtaagt tacatgcact ggtaccagca gaagtcaggc | | | | 120 |
| acctccccca aaagatggat ttatgacaca tccaaactgg cttctggagt ccctgctcgc | | | | 180 |
| ttcagtggca gtgggtctgg gacctcttat tctctcacaa tcagcagcat ggaggctgaa | | | | 240 |
| gatgctgcca cttattactg ccagcagtgg agtagtaacc cgctcacgtt cggtgctggg | | | | 300 |
| accaagctgg agctgaaacg t | | | | 321 |

<210> SEQ ID NO 11
<211> LENGTH: 351
<212> TYPE: DNA
<213> ORGANISM: Mus sp.

<400> SEQUENCE: 11

| | | | | |
|---|---|---|---|---|
| gaggttcagc tgcagcagtc tggggcagag cttgtgaagc caggggcctc agtcaagttg | | | | 60 |
| tcctgcacag cttctggctt caacattaaa gactacttta cactgggt gaaccagagg | | | | 120 |
| actaaacagg gcctggagtg gattggaagg attgatcctg aggatggtga aactaaatat | | | | 180 |
| gccccgaaat tccagggcaa ggccacttta acagcagaca caacctccaa cacagccgac | | | | 240 |
| cttcagctca gcagtctgac atctgaggac actgccgtct attactgcgt tctttactac | | | | 300 |
| agtcgaagct ttgactactg gggccaaggc accactctca cagtctcctc a | | | | 351 |

```
<210> SEQ ID NO 12
<211> LENGTH: 324
<212> TYPE: DNA
<213> ORGANISM: Mus sp.

<400> SEQUENCE: 12
gacatcttgc tgactcagtc tccagccatc ctgtctgtga gtccaggaga aagagtcagt      60
ttctcctgca gggccagtca gagcattggc acaagcatac actggtatca gcaaagaaca     120
aatggttctc caaggcttct cataaagtat gcttctgagt ctatctctgg gatcccttcc     180
aggtttagtg gcagtggatc agggacagat tttactctta gcatcaatag tgtggagtct     240
gaagatattg cagattatta ctgtcaacaa agtaatagat ggccattcac gttcggctcg     300
gggacaaagt tggaaataaa acgt                                           324

<210> SEQ ID NO 13
<211> LENGTH: 357
<212> TYPE: DNA
<213> ORGANISM: Mus sp.

<400> SEQUENCE: 13
gaggttcagc tgcagcagtc tggggcagag tttgtgaagc caggggcctc agtcaagttg      60
tcctgcagag tttctggctt caacattaag gactactata ttaactgggt gaagcagagg     120
actgaacagg gcctggagtg gattggaagg attgatcctg aggatggtga aactaaatat     180
gccccgaaat tccagggcaa ggccactata acagcagaca catcctccaa cacagccaac     240
ctgcacctca gcagcctgac atctgcggac actgccgtct attactgtgc tagctcaggc     300
tacgcctttg cctggtttct ttactggggt caagggactc tggtcactgt ctctgca       357
```

REAGENTS, METHODS, AND SYSTEMS FOR DETECTING METHICILLIN-RESISTANT *STAPHYLOCOCCUS*

CROSS-REFERENCE

This application is a national stage of International Appl. No. PCT/US2009/043143, filed May 7, 2009 which claims priority to U.S. Provisional Application Ser. No. 61/126,831 filed May 7, 2008 and to U.S. Provisional Application Ser. No. 61/092,267 filed Aug. 27, 2008, all of which are hereby incorporated by reference in their entirety.

FIELD OF THE INVENTION

The present invention relates to the field of diagnostics and treatment, including the detection of pathogens, and particularly to the detection of methicillin-resistant *Staphylococcus aureus* (MRSA).

BACKGROUND

*Staphylococcus aureus* is a gram positive bacterium and a common cause of nosocomial infections. Certain strains of *Staphylococcus aureus* are highly resistant to methicillin and related antibiotics due to the acquisition of the mecA gene, which encodes Penicillin Binding Protein 2a (PBP2a). These antibiotic resistant strains are known as Methicillin-Resistant *Staphylococcus aureus*, or MRSA, and their quick detection in samples is highly desirable for guiding effective patient therapy, and for preventing the spread of antibiotic resistant bacteria from infected patients or materials.

PBP2a prevents the binding of beta-lactam antibiotics, such as penicillins and cephalosporins, to mecA-encoding *Staphylococcus*, thereby conferring antibiotic resistance. Accurate and sensitive immunodetection of methicillin-resistant *staphylococcus*, including MRSA, via the presence of PBP2a, for example in a biosensor system, requires high-affinity and highly specific binding reagents. For example, Protein A, which is a protein produced by *Staphylococcus aureus*, and which is not associated with antibiotic resistance, has broad antibody- (e.g., IgG-) binding properties. In addition, for sensitive detection, PBP2a-binding agents are ideally directed against exposed regions or epitopes of PBP2a on intact or lysed cells, so as to allow sensitive detection of PBP2a.

Reagents, methods and systems for detecting antibiotic-resistant *staphylococcus*, including MRSA, in samples are needed, including high affinity and/or selective immunoreagents, as well as accurate and sensitive detection systems.

SUMMARY

The present invention provides PBP2a peptide antigens for generating antibodies against MRSA, and provides high-affinity binding agents (antibodies) that detect MRSA by selective immunoreactivity with PBP2a. The antibodies are useful in methods and systems for detecting MRSA, including biosensor systems as described herein, or as components of diagnostic or detection kits. The antibodies, in some embodiments, have therapeutic value against MRSA infection.

In one aspect, the present invention provides polypeptide antigens for generating antibodies against PBP2a of MRSA, as well as encoding polynucleotides and cells expressing the same. The polypeptide antigens consist essentially of, or consist of, the amino acid sequence of SEQ ID NO:1, or SEQ ID NO:1 with one or two amino acid modifications. SEQ ID NO:1 is amino acids 27 to 41 of *Staphylococcus aureus* PBP2a, and is an extracellularly exposed epitope that is sufficiently available on intact cells for antibody binding.

In a second aspect, the present invention provides antibodies and antigen-binding fragments that selectively bind PBP2a or MRSA. In various embodiments, the antibodies and antigen-binding fragments bind selectively to PBP2a over other antigens normally present on *Staphylococcus aureas* (such as Protein A, for example), and bind to PBP2a with high affinity. Such binding reagents are thus useful for detecting methicillin-resistant *staphylococcus* (e.g., selectively over other antibiotic-sensitive *staphylococcus* that may be present). The antibodies of the invention may be used in connection with biosensor systems.

In one embodiment, the antibodies and antigen-binding fragments selectively bind to the amino acid sequence of SEQ ID NO:1. For example, in accordance with this embodiment, the antibodies and antigen-binding fragments can be produced or raised against PBP2a using the polypeptide antigen of SEQ ID NO:1 (or as modified) as an immunogen, or alternatively by selection of antibody variable domains from a phage library.

In another embodiment, the antibodies and antigen-binding fragments bind to a PBP2a epitope defined by the binding of an antibody comprising the light chain amino acid sequence of SEQ ID NO:2 and the heavy chain amino acid sequence of SEQ ID NO:3. Alternatively, the antibodies and antigen-binding fragments bind to a PBP2a epitope as defined by an antibody comprising the light chain amino acid sequence of SEQ ID NO:4 and the heavy chain amino acid sequence of SEQ ID NO:5. Alternatively still, the antibody and antigen-binding fragments may bind a PBP2a epitope as defined by the binding of an antibody comprising the light chain amino acid sequence of SEQ ID NO:6 and the heavy chain amino acid sequence of SEQ ID NO:7. The antibodies and antibody fragments may comprise at least one light chain CDR or at least one heavy chain CDR, or a complete set of heavy chain CDRs and/or light chain CDRs as shown in Table 1. The antibodies may comprise a light chain and/or heavy chain of antibody 2B2, 2G7, or 3B12, which are described herein.

The antibodies of the invention may bind PBP2a with high affinity, such as, in some embodiments, a dissociation constant (Kd) of about $1 \times 10^{-9}$ M, or higher. The Kd may be determined by any suitable method, such as, for example, ELISA or surface plasmon resonance (e.g., BIACORE™, Biacore, Inc., Piscataway, N.J.).

In another aspect, the invention provides methods and systems for the detection of methicillin-resistant *staphylococcus*, e.g., via the detection of PBP2a, with the antibodies or antibody fragments of the present invention. The methods and systems involve contacting a sample suspected of comprising methicillin-resistant *staphylococcus* (e.g. MRSA), with at least one antibody or antigen-binding fragment of the invention. Such samples include various body fluids and tissue specimens including skin, wound, ulcer, or burn debris, scrapings, or swabbings (e.g., nasal and/or throat), and including blood, serum, sputum, pus, wound drainage, and tissue scrapings, among others. In accordance with this aspect, a positive detection of PBP2a, e.g., the presence of PBP2a, indicates the presence of methicillin-resistant *staphylococcus*. In some embodiments, the co-localization of Protein A on PBP2a-expressing cells indicates the presence of MRSA. For example, bacteria expressing Protein A on their surface (*Staphylococcus aureus*) may be captured, immobilized, and/or isolated (for example, with antibodies against Protein A), and this captured, immobilized, or isolated population tested for the presence of PBP2a, to thereby indicate the presence of MRSA.

The systems for the detection of PBP2a, methicillin-resistant *staphylococcus*, or MRSA may employ conventional ELISA or lateral flow chromatographic formats, or may involve a biosensor able to recognize target antigens in a sample, and in a short time. In some embodiments, the invention employs the BIOFLASH™ biosensor system.

The present invention further provides kits for the detection of PBP2a, so as to detect methicillin-resistant *staphylococcus*, including MRSA. The detection kit can comprise one or more containers, a plurality of which contain an antibody or antibody fragment of the invention (e.g., in lyophilized or solution form), and where at least one antibody in the kit is labeled for detection. In certain embodiments, the kit further includes antibodies against Protein A. The kit may further comprise the reagents necessary to perform an immunodetection assay, such as ELISA.

The invention also provides the antibody and antibody fragments of the invention as pharmaceutical compositions, that is, formulated for administration to a patient. Antibodies or fragments of the invention, in some embodiments, have therapeutic utility against MRSA infection.

BRIEF DESCRIPTION OF THE DRAWINGS

FIG. 6 shows data from serial dilution tests of a CANARY® assay (Innovative Biosensors, Inc., Rockville, Md.) using antibody 2G7 with recombinant PBP2a.

DETAILED DESCRIPTION

Figure 1:
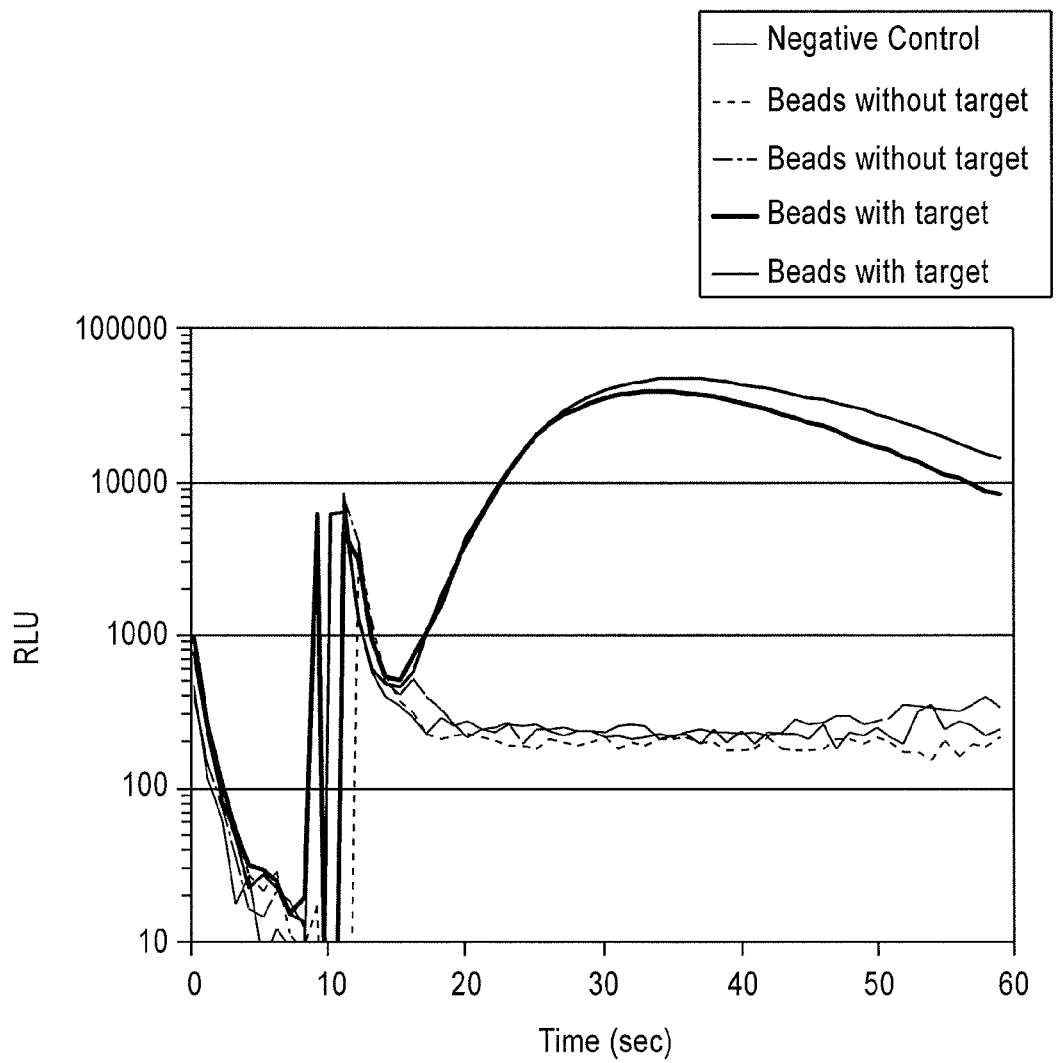
FIG. 1 is a plot of luminometer response readings for samples with and without PBP2a that were exposed to CANARY® platform sensor cells.

The present invention provides reagents, such as PBP2a peptide antigens for generating antibodies against PBP2a, and high-affinity antibodies that detect methicillin-resistant *staphylococcus* by selective immunoreactivity with PBP2a. The antibodies are useful in methods and systems for detecting MRSA, including biosensor systems as described herein, or as components of diagnostic or detection kits. The antibodies, in some embodiments, have therapeutic value against MRSA infection.

PBP2a Antigens and Epitopes

The present invention provides antigen fragments and epitopes for generating PBP2a-specific and/or MRSA-specific antibodies. Such antibodies may recognize PBP2a selectively over Protein A, or other epitopes of *S. aureas* that are not associated with antibiotic resistance, thereby providing selective recognition of MRSA over other antibiotic-sensitive Staphylococci that may be present. The antigen fragments of the invention consist essentially of, or consist of, the amino acid sequence of SEQ ID NO:1, optionally modified as described below. The term "consists essentially of" in this context provides for the inclusion of other amino acid sequences at the N- and/or C-terminus of SEQ ID NO:1 that are not present in the wild-type PBP2a protein. That is, the PBP2a antigen fragments include recombinant fusion with other non-PBP2a amino acid sequences. Alternatively, additional wild-type PBP2a sequences may be added to the N- and/or C-terminus, such as from 1 to 5 amino acids, or from 1 to 3 amino acids, so long as the essential antigenic or epitopic character of SEQ ID NO:1 is not substantially affected.

The amino acid sequence of SEQ ID NO:1 includes amino acids 27 to 41 of *Staphylococcus aureus* protein PBP2a (i.e., amino acid sequence DKEINNTIDAIEDKN (SEQ ID NO:1) from accession number CAA74376, which is hereby incorporated by reference). When integrated into a MRSA cell wall, a portion of PBP2a containing SEQ ID NO:1 extends extracellularly and is available for antibody binding. Thus, an epitope within the peptide defined by SEQ ID NO:1 provides a means for recognizing the presence of PBP2a and, by association, methicillin-resistant staphylococcus, in a sample.

In certain embodiments, the PBP2a antigen fragment contains one or two amino acid modifications with respect to SEQ ID NO:1. In this context, an amino acid modification is an amino acid insertion, substitution, or deletion with respect to SEQ ID NO:1. An amino acid substitution can be conservative, i.e., a hydrophobic amino acid for a hydrophobic amino acid, or non-conservative. Combinations of the different types of modifications are possible when two amino acid modifications (e.g., insertion, deletion, and/or substitution) are present.

The PBP2a antigen fragments of the invention are useful, for example, in producing or selecting antibodies or antibody fragments that will recognize PBP2a/MRSA. For example, the PBP2a antigen fragments of the invention may be used as immunogens to produce polyclonal or monoclonal antibodies against PBP2a, which are useful in the methods and systems described herein. Alternatively, the PBP2a antigen fragments may be used to select PBP2a binding sequences from an antibody library, as described in more detail herein.

Antibodies and Reagents for Detecting PBP2a/MRSA

The present invention provides antibodies and antibody fragments (or binding agents) useful in the recognition of PBP2a/methicillin-resistant *staphylococcus*, including those that selectively bind to, or were raised against the recombinant PBP2a or PBP2a antigen fragments described herein. Particularly, the antibodies and antigen-binding fragments bind selectively to PBP2a over other antigens normally present on *Staphylococcus aureas* (such as Protein A, for example), and bind with high affinity. The antibodies and antibody fragments in accordance with the invention can be monoclonal, polyclonal, and/or chimeric (including, for example, humanized).

The antibodies of the invention may have a binding affinity (Kd) of about $1 \times 10^{-9}$ M or higher. For example, the antibody may have a Kd of at least about 1 to $5 \times 10^{-10}$ M, or at least about 1 to $5 \times 10^{-12}$ M. The Kd may be determined using any suitable method, such as ELISA or SPR (e.g., BIACORE™).

The antibodies bind to PBP2a, such as PBP2a on the surface of methicillin resistant *staphylococcus*, so as to distinguish drug-resistant *staphylococcus* from other drug-sensitive *staphylococcus* that may be present. Thus, the antibodies bind selectively to PBP2a, to exposed and/or available epitopes, selectively over other *S. aureus* antigens that may be present, and which are not associated with MRSA (e.g., Protein A).

In one embodiment, the antibodies and antigen-binding fragments selectively bind to the amino acid sequence of SEQ ID NO:1, optionally having one or two amino acid modifications. For example, in accordance with this embodiment, the antibodies and antigen-binding fragments can be produced or raised against PBP2a using the polypeptide antigen of SEQ ID NO:1 (or as modified) as an immunogen, or alternatively by selection of antibody variable domains from a library, e.g., a phage-display library.

In other embodiments, the antibodies bind to an epitope defined by the binding of an antibody having a light chain amino acid sequence (VL) comprising SEQ ID NO:2 and a heavy chain amino acid sequence (VH) comprising SEQ ID NO:3 (e.g. antibody 2B2); or an antibody having a light chain amino acid sequence (VL) comprising SEQ ID NO:4 and a heavy chain amino acid sequence (VH) comprising SEQ ID NO:5 (e.g. antibody 2G7); or an antibody having a light chain amino acid (VL) sequence comprising SEQ ID NO:6 and a heavy chain amino acid sequence (VH) comprising SEQ ID NO:7 (e.g. antibody 3B12). Such antibodies may be selected based on the ability to compete with binding of 2B2, 2G7, or 3B12 to PBP2a in a competitive binding assay. Specifically, a sample comprising the antibody defining the epitope can be used to saturate binding to an epitope of PBP2a. A second antibody, whose epitope is to be determined, is then contacted with the antibody-bound PBP2a. Binding of the second antibody can be detected by an increase in relative signal units, and if detected, indicates binding to an epitope unique from the epitope bound by the first antibody. However, if the epitope for this antibody is already saturated by a previous antibody, then an increase in relative signal units is not observed.

The antibody or fragment may comprise one, two, or three CDRs, or a full set of CDRs as set forth in a heavy chain fragment and/or light chain fragment of SEQ ID NOS:2-7. The portions of each sequence representing a complementarity determining region (CDR) are underlined in SEQ ID NOS:2-7 below (also see Table 1). An antigen binding site is generally formed by the variable heavy (VH) and variable light (VL) immunoglobulin domains, with the antigen-binding interface formed by six surface polypeptide loops, termed complimentarity determining regions (CDRs). There are three CDRs in each VH (HCDR1, HCDR2, HCDR3) and in each VL (LCDR1, LCDR2, LCDR3), together with framework regions (FRs). As described herein, a "set of CDRs" comprises CDR1, CDR2 and CDR3. Thus, a set of HCDRs refers to HCDR1, HCDR2 and HCDR3, and a set of LCDRs refers to LCDR1, LCDR2 and LCDR3. Unless otherwise stated, a "set of CDRs" includes HCDRs and LCDRs.

The binding agent of the invention normally comprises an antibody VH and/or VL domain. A VH domain of the invention comprises a set of HCDRs, and a VL domain comprises a set of LCDRs. An antibody molecule may comprise an antibody VH domain comprising a VH CDR1, CDR2 and CDR3 and a framework. It may alternatively or also comprise an antibody VL domain comprising a VL CDR1, CDR2 and CDR3 and a framework. As described herein, an antibody, or antibody fragment (or "binding agent") of the invention may comprise an antigen-binding site within a non-antibody molecule, normally provided by one or more CDRs e.g. a set of CDRs in a non-antibody protein scaffold, as discussed further below.

In certain embodiments, the antibody may comprise the amino acid sequence of SEQ ID NO:2, SEQ ID NO:3, or both SEQ ID NOS: 2 and 3, or it may comprise the amino acid sequence of SEQ ID NO:4, SEQ ID NO:5, or both SEQ ID NOS: 4 and 5, or it may comprise the amino acid sequence of SEQ ID NO:6, SEQ ID NO:7, or both SEQ ID NOS: 6 and 7. The amino acid sequences for SEQ ID NOS: 2-7 are listed below. The portions of each sequence representing a complementarity determining region (CDR) are underlined. Alternatively, the antibody variable region, e.g., heavy and/or light chain, may comprise an amino acid sequence of SEQ ID NOS:2-7, optionally having from 1 to 10 amino acid deletions, insertions, and/or substitutions (collectively), such as from 1 to 5 amino acid deletions, insertions, and/or substitutions (e.g, 1, 2, or 3). Such amino acid substitutions, deletions, or insertions in some embodiments are confined to regions outside the CDRs, or alternatively, include modifications within CDRs.

Among the six short CDR sequences, the third CDR of the heavy chain (HCDR3) has a greater size variability (greater diversity essentially due to the mechanisms of arrangement of the genes which give rise to it). It may be as short as 2 amino acids although the longest size known is 26. CDR length may also vary according to the length that can be accommodated by the particular underlying framework. Functionally, HCDR3 plays a role in part in the determination of the specificity of the antibody.

```
2B2Variable light:
                                            (SEQ ID NO: 2)
DILLTQSPAILSVSPGERVSFSCRASQSIGTSIHWYQQRTNGSPRLLIKY

ASESISGIPSRFSGSGSGTDFTLSINSVESEDIADYYCQQSNRWPFTFGS

GTKLEIKR

2B2Variable Heavy:
                                            (SEQ ID NO: 3)
EVQLQQSGAEFVK/RPGASVKLSCRVSGFNIKDYYINWVKQRTEQGLEWI

GRIDPEDGETKYAPKFQGKATITADTSSNTANLHLSSLTSADTAVYYCAS

SGYAFAWFLYWGQGTLVTVSA

2G7Variable Light:
                                            (SEQ ID NO: 4)
QNVLTQSPAIMSASPGEKVTMTCSASSSVSYMHWYQQKSGTSPKRWIYDT

SKLASGVPARFSGSGSGTSYSLTISSMEAEDAATYYCQQWSSNPLTFGAG

TKLELKR

2G7Variable Heavy:
                                            (SEQ ID NO: 5)
EVQLQQSGAELVKPGASVKLSCTASGFNIKDYFIHWVNQRTKQGLEWIGR

IDPEDGETKYAPKFQGKATLTADTTSNTADLQLSSLTSEDTAVYYCVLYY

SRSFDYWGQGTTLTVSS

3B12Variable Light:
                                            (SEQ ID NO: 6)
DILLTQSPAILSVSPGERVSFSCRASQSIGTSIHWYQQRTNGSPRLLIKY

ASESISGIPSRFSGSGSGTDFTLSINSVESEDIADYYCQQSNRWPFTFGS

GTKLEIKR

3B12Variable Heavy:
                                            (SEQ ID NO: 7)
EVQLQQSGAEFVKPGASVKLSCRVSGFNIKDYYINWVKQRTEQGLEWIGR

IDPEDGETKYAPKFQGKATITADTSSNTANLHLSSLTSADTAVYYCASSG

YAFAWFLYWGQGTLVTVSA
```

TABLE 1

Complementarity Determining Region (CDR) of PBP2a antibodies

| Antibodies | Complementarity Determining Region (CDR) | | |
|---|---|---|---|
| | 1 | 2 | 3 |
| 2B2 Variable Light | QSIGTS (Residues 27-32 of SEQ ID NO:2) | YAS | QQSNRWPFT (Residues 89-97 of SEQ ID NO:2) |
| 2B2 Variable Heavy | GFNIKDYY (Residues 27-34 of SEQ ID NO:3) | IDPEDGET (Residues 52-59 of SEQ ID NO:3) | ASSGYAFAWFLY (Residues 98-109 of SEQ ID NO:3) |
| 2G7 Variable Light | SSVSY (Residues 27-31 of SEQ ID NO:4) | DTS | QQWSSNPLT (Residues 88-96 of SEQ ID NO:4) |
| 2G7 Variable Heavy | GFNIKDYF (Residues 26-33 of SEQ ID NO:5) | IDPEDGET (Residues 51-58 of SEQ ID NO:5) | VLYYSRSFDY (Residues 97-106 of SEQ ID NO:5) |
| 3B12 Variable Light | QSIGTS (Residues 27-32 of SEQ ID NO:6) | YAS | QQSNRWPFT (Residues 89-97 of SEQ ID NO:6) |
| 3B12 Variable Heavy | GFNIKDYY (Residues 26-33 of SEQ ID NO:7) | IDPEDGET (Residues 51-58 of SEQ ID NO:7) | ASSGYAFAWFLY (Residues 97-108 of SEQ ID NO:7) |

Typically, a VH domain is paired with a VL domain to provide an antibody antigen-binding site, although as discussed further below a VH or VL domain alone may be used to bind antigen. An antibody VH domain (e.g., of 2B2, 2G7, or 3B12) may be paired with an antibody VL domain (e.g., independently selected from 2B2, 2G7, or 3B12), so that an antibody antigen-binding site is formed comprising both the antibody VH and VL domains. VL light-chain promiscuity is well established in the art.

A binding agent in accordance with the invention may comprise an antibody molecule having one or more CDRs, e.g. a set of CDRs, within an antibody framework. For example, one or more CDRs or a set of CDRs of an antibody may be grafted into a framework (e.g. human framework) to provide an antibody molecule. The framework regions may be of human germline gene sequences, or be non-germlined. Thus, the framework may be germlined where one or more residues within the framework are changed to match the residues at the equivalent position in the most similar human germline framework. Thus, a binding member of the invention may be an isolated human antibody molecule having a VH domain comprising a set of HCDRs in a human germline framework, e.g. human germline IgG VH framework. The binding member also has a VL domain comprising a set of LCDRs, e.g. in a human germline IgG VL framework.

Although CDRs can be carried by non-antibody scaffolds, the structure for carrying a CDR or a set of CDRs of the invention will generally be an antibody heavy or light chain sequence or substantial portion thereof in which the CDR or set of CDRs is located at a location corresponding to the CDR or set of CDRs of naturally occurring VH and VL antibody variable domains encoded by rearranged immunoglobulin genes. The structures and locations of immunoglobulin variable domains may be determined by reference to the Kabat numbering system.

Binding agents of the present invention may further comprise antibody constant regions or parts thereof, e.g. human antibody constant regions or parts thereof. For example, a VL domain may be attached at its C-terminal end to antibody light chain constant domains including human Cκ or Cλ chains. Similarly, a binding agent based on a VH domain may be attached at its C-terminal end to all or part (e.g. a CH1 domain) of an immunoglobulin heavy chain derived from any antibody isotype, e.g. IgG, IgA, IgE and IgM and any of the isotype sub-classes, particularly IgG1 and IgG2.

Forms of Antibodies

Antibody molecule refers to an immunoglobulin whether natural or partly or wholly synthetically produced. The term also covers any polypeptide or protein comprising an antibody antigen-binding site. Antibody fragments that comprise an antibody antigen-binding site include, but are not limited to, molecules such as Fab, Fab', Fab'-SH, scFv, Fv, dAb and Fd. Various other antibody molecules including one or more antibody antigen-binding sites have been engineered, including for example $Fab_2$, $Fab_3$, diabodies, triabodies, tetrabodies and minibodies.

It is possible to take monoclonal and other antibodies and use techniques of recombinant DNA technology to produce other antibodies or chimeric molecules that bind the target antigen. Such techniques may involve introducing DNA encoding the immunoglobulin variable region, or the CDRs, of an antibody to the constant regions, or constant regions plus framework regions, of a different immunoglobulin. A hybridoma or other cell producing an antibody may be subject to genetic mutation or other changes, which may or may not alter the binding specificity of antibodies produced.

The antibodies and antibody fragments include whole antibodies and antigen-binding fragments thereof. Antibody fragments include single chain fragments, Fv fragments, single chain Fv fragments, and Fab fragments. Fab is a double chain binding fragment of an intact antibody, and having at least substantially complete light and heavy chain variable domains sufficient for antigen-specific bindings, and parts of the light and heavy chain constant regions sufficient to maintain association of the light and heavy chains (e.g., including Fab' and $F(ab')_2$ fragments). Fab fragments can be formed by complexing a full-length or substantially full-length light chain with a heavy chain comprising the variable domain and at least the CH1 domain of the constant region. While various antibody fragments can be obtained by digesting an antibody, one of skill in the art will appreciate that such fragments can be synthesized de novo either chemically or by utilizing recombinant DNA methodology. Thus, the antibody and antibody fragments of the invention include antibody fragments either produced by the modification of whole antibodies or those synthesized de novo using recombinant DNA methodologies (e.g., single chain Fv).

Methods for producing single chain antibodies are described, for example, in U.S. Pat. No. 4,946,778. Techniques for the construction of Fab expression libraries are described by Huse et al., *Science* (1989) 246:1275-1281; these techniques facilitate rapid identification of monoclonal Fab fragments and can be used to detect monoclonal Fab fragments with the desired specificity for PBP2a, or an epitope as described above. Suitable antibodies and antibody fragments include those that are obtained using methods such as phage display.

Also provided are single chain antibodies having one heavy chain (e.g., a heavy chain as described above) and one light chain (e.g., a light chain as described above). Single chain antibodies include fusion proteins of light and heavy chains, generally with a spacer protein between the light and heavy chains. For example, the single chain antibody may bind an epitope of PBP2a as defined by an antibody as described above. For example, the single chain amino acid may have a light chain amino acid sequence comprising SEQ ID NO:2 and a heavy chain amino acid sequence comprising SEQ ID NO:3; or a light chain amino acid sequence comprising SEQ ID NO:4 and a heavy chain amino acid sequence comprising SEQ ID NO:5; or a light chain amino acid sequence with SEQ ID NO:6 and a heavy chain amino acid sequence with SEQ ID NO:7. Examples of such fusion proteins include single chain antibodies including SEQ ID NOs:2 or 3 or both SEQ ID NOs 2 and 3, SEQ ID NOs:4 or 5 or both SEQ ID NOs 4 and 5, or SEQ ID NOs:6 or 7 or both SEQ ID NOs 6 and 7. Examples also include light and heavy chains comprising one or more or all of the CDRs from SEQ ID NOs:2 or 3 or both SEQ ID NOs 2 and 3, SEQ ID NOs:4 or 5 or both SEQ ID NOs 4 and 5, or SEQ ID NOs: 6 or 7 or both SEQ ID NOs 6 and 7. The single chain antibodies may comprise one or a combination of heavy chain and/or light chain CDRs as shown in Table 1, above.

The antibody can be a monoclonal antibody, a polyclonal antibody, or a chimeric antibody (including, for example, a humanized antibody). Optionally, the antibody specifically binds to, or was raised against the PBP2a antigen to be detected.

Monoclonal antibodies are prepared from hybridoma cells secreting the desired antibody and screening methods are known in the art and examples are described below. Monoclonal antibodies can be prepared by any technique that provides for the production of antibody molecules by continuous cell lines in culture, including the hybridoma technique originally developed by Kohler and Milstein ((1975) *Nature* 256: 495-497), as well as the trioma technique, the human B-cell hybridoma technique (Kozbor et al. (1983) *Immunology Today* 4:72), and the EBV-hybridoma technique to produce human monoclonal antibodies (Cole et al., *Monoclonal Antibodies and Cancer Therapy*, Alan R. Liss, Inc., pp. 77-96, 1985). Monoclonal antibodies also can be produced in germ-free animals as was described in U.S. Pat. No. 5,091,512. The antibodies and antibody fragments can be humanized or fully human (i.e., produced by transgenic animals that make human antibodies).

Polyclonal antibodies can be prepared by immunizing a suitable animal with the antigen (e.g., recombinant PBP2a or the peptide of SEQ ID NO:1 as described) to be detected. The cells producing antibody molecules directed against the antigen can be isolated from the animal (e.g., from the blood) and, optionally, further purified by well-known techniques, such as panning against an antigen-coated petri dish. Modifications can be utilized as desired to select for surface antibodies rather than secreted antibodies.

Chimeric antibodies are antibodies generally made using recombinant technology. Such antibodies can comprise one or more of the complementarity determining regions of one antibody and one or more framework regions of another antibody. One example of a chimeric antibody is a humanized antibody. Thus, a chimeric antibody can include one or more or all of the complementarity determining regions (CDR) of the protein sequence of antibodies or antibody fragments that selectively bind to, or were raised against polypeptide having amino acid sequence SEQ ID NO:1, or can include one or more or all of the CDRs of SEQ ID NO:2, SEQ ID NO:3, SEQ ID NO:4, SEQ ID NO:5, SEQ ID NO:6 or SEQ ID NO:7, or both SEQ ID NO:2 and 3, both SEQ ID NO:4 and 5, or both SEQ ID NO:6 and 7. The framework regions of the chimeric antibody can be from a different antibody or a different species (e.g., human).

Any of the many well known protocols used for fusing lymphocytes and immortalized cell lines can be applied for the purpose of generating a cell producing a surface monoclonal antibody (see, e.g., Current Protocols in Immunology, supra; Galfre et al., Nature 266:55052, 1977; Kenneth, In Monoclonal Antibodies: A New Dimension In Biological Analyses, Plenum Publishing Corp., New York, N.Y., 1980; and Lerner, Yale J Biol Med 54:387-402 (1981). Moreover, the ordinarily skilled worker will appreciate that there are many variations of such methods which also would be useful.

As an alternative to preparing monoclonal cells, a nucleic acid encoding a monoclonal antibody heavy and light chain can be identified and isolated by screening a recombinant combinatorial immunoglobulin library (e.g., an antibody phage display library) with the antigen to thereby isolate immunoglobulin library members that bind the antigen. Kits for generating and screening phage display libraries are commercially available. Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication WO 92/20791; PCT Publication No. WO 92/15679; PCT Publication WO 93/01288; PCT Publication No. WO 92/01047; PCT Publication No. WO 92/09690; PCT Publication No. WO 90/02809; Fuchs et al., Bio/Technology 9:1370-1372 (1991); Hay et al., Human Antibody Hybridomas 3:81-85 (1992); Huse et al., Science 246:1275-1281 (1989); Griffiths et al., EMBO J. 12:725-734 (1993).

After the desired member of the library is identified, the specific sequence can be cloned into any suitable nucleic acid vector and transfected or otherwise injected into a cell such as a fibroblast. Thus provided herein is a nucleic acid vector encoding the light and/or heavy chain of an antibody or fragment disclosed herein. The vector can also encode amino acids operably linked to the antibody sequence as appropriate for the cell which is to express the antibody. As discussed above, the cytoplasmic transmembrane sequence of a fibroblast growth factor receptor can be linked to a single-chain antibody specific for the antigen to be detected, so that the cell immobilizes calcium when contacted with the antigen. Although separate recombinant light chains (e.g., SEQ ID NO:2 or 4 or 6) and heavy chain (e.g., SEQ ID NO:3 or 5 or 7) can be expressed in the fibroblasts to form the chimeric antibody, single chain antibodies also are suitable (see, e.g., Bird et al., Trends Biotechnol 9:132-137, 1991; and Huston et al., Int Rev Immunol 10:195-217, 1993).

The antibodies and antibody fragments described can be screened for binding to PBP2a, or epitope thereof. The terms bind, binds, and binding, when referring to an antibody or other binding moiety, indicate a binding reaction or affinity that is determinative of the presence of a target antigen. Thus, under designated assay conditions, the specified binding moieties bind preferentially to a particular target antigen and do not bind in a significant amount to other components present in a test sample. Epitopes include any determinant capable of specific interaction with the described antibodies. Epitopic determinants usually consist of chemically active surface groupings of molecules such as amino acids or sugar side chains and usually have specific three dimensional structural characteristics, as well as specific charge characteristics.

A variety of immunoassay formats may be used to select antibodies that are specifically immunoreactive with a particular epitope. For example, solid-phase ELISA immunoassays are routinely used to select monoclonal antibodies specifically immunoreactive with an antigen. Typically a specific or selective reaction is at a statistically significant level above the background signal. For example, at least 1.5 or twice the background signal or noise or more than 10 to 100 times the background signal or noise. Specific binding between an antibody or other binding agent and an antigen generally means a binding affinity (e.g., Kd dissociation constant (Kd)) of at least about $10^6$ M$^{-1}$. Further examples of specific binding affinity include, but are not limited to, at least about $10^7$ M$^{-1}$, at least about $10^8$ M$^{-1}$, at least about $10^9$ M$^{-1}$, and at least about $10^{10}$ M$^{-1}$. Specific binding between an antibody or other binding agent and an antigen can be described in terms of their dissociation constant Kd. The antibodies and antibody fragments described can bind with a Kd of at least 1 μM, at least 500 nM, at least 300 nM, at least 100 nM, at least 50 nM, at least 30 nM, at least 10 nM, or at least 3 nM, or at least 1 nM, or at least 0.5 nM.

The antibody (or a fragment thereof) can be conjugated to a selection moiety. A selection moiety is any marker or composition that can be used to selectively isolate cells and/or capture compounds bound by an antibody or fragment conjugate. A selection moiety can be any marker or composition that can be used to selectively isolate cells and/or capture compounds bound by an antibody or fragment conjugate. The selection moiety can be a solid matrix. For example, a solid matrix can include, but is not limited to plates, slides, dishes, beads, particles, cups, stands and chips. The selection moiety can be paramagnetic, fluorescent, or the like. For example, the selection moiety can be a paramagnetic or fluorescent bead or composition. When such a paramagnetic antibody conjugate is bound to a cell, for example, is bound to PBP2a of a cell, application of a magnetic field to the sample can be used to selectively isolate the cell bound with the conjugate. In one example, a preformed solid surface conjugated anti-PBP2a antibody is mixed with a sample and incubated with shaking. The methicillin-resistant *staphylococcus* cells in the sample are absorbed by the solid-antibody conjugate. A magnetic force can be applied and wash can be performed to remove other bacteria or cells not adsorbed to the PBP2a specific antibody conjugate. Similarly, cell bearing an antibody conjugate with a fluorescent moiety can be selectively isolated using fluorescence cell sorting procedures. The selection moiety can be attached or conjugated to an antibody (or antibody fragment) using any method. Such methods include, but not limited to the biotinylated antibody and streptavidin bead based conjugation, carboxyl bead based conjugation, carbonate-bi carbonate mediated adsorption.

The described antibodies and fragments can be labeled with a detectable moiety or marker. Optionally, the detectable marker is selected from a fluorescent moiety, an enzyme linked moiety, a biotinylated moiety and a radiolabeled moiety. By label or detectable moiety is meant any detectable tag that can be attached directly (e.g., a fluorescent molecule integrated into a polypeptide or nucleic acid) or indirectly (e.g., by way of binding to a primary antibody with a secondary or tertiary antibody with an integrated fluorescent molecule) to the molecule of interest. Thus, a label or detectable moiety is any tag that can be visualized with imaging methods. The detectable tag can be a radio-opaque substance, a radiolabel, a fluorescent label, or a magnetic label. The detectable tag can be selected from the group consisting of gamma-emitters, beta-emitters, alpha-emitters, positron-emitters, X-ray-emitters and fluorescence-emitters suitable for localization. Suitable fluorescent compounds include fluorescein sodium, fluorescein isothiocyanate, phycoerythrin, and Texas Red sulfonyl chloride. See, de Belder & Wik (Preparation and properties of fluorescein-labeled hyaluronate. Carbohydr. Res. 44(2):251-57 (1975). Those skilled in the art will know, or will be able to ascertain with no more than routine experimentation, other fluorescent compounds that are suitable for labeling the molecule.

Polynucleotides and Cells

The present invention also provides polynucleotides that encode an antibody of the invention as described above. The polynucleotide may encode a light chain and/or heavy chain of SEQ ID NOS:2-7, as described above. Examples of such light chain nucleic acid sequences include SEQ ID NO:8, 10 and 12, and examples of such heavy chain nucleic acid sequences include SEQ ID NO:9, 11 and 13. Also provided are nucleic acids that encode one or more or all (e.g., a set) of the complementarity determining regions of SEQ ID NO: 2, 3, 4, 5, 6 and 7 (listed in Table 1) or combinations thereof. Exemplary polynucleotides are shown below. The underlined portions of each sequence represents regions encoding the CDRs of the antibodies.

2B2Variable Light:
(SEQ ID NO: 8)
5'GACATCTTGCTGACTCAGTCTCCAGCCATCCTGTCTGTGAGTCCAGGA GAAAGAGTCAGTTTCTCCTGCAGGGCCAGT<u>CAGAGCATTGGCACAAGCAT ACACTGGTATCAGCAAAGAACAAATGGTTCTCCAAGGCTTCTCATAAAGT</u>

<u>ATGCTTCT</u>GAGTCTATCTCTGGGATCCCTTCCAGGTTTAGTGGCAGTGGA

TCAGGGACAGATTTTACTCTTAGCATCAATAGTGTGGAGTCTGAAGATAT

TGCAGATTATTACTGT<u>CAACAAAGTAATAGATGGCCATTCACG</u>TTCGGCT

CGGGGACAAAGTTGGAAATAAAACGG-3'

2B2Variable Heavy:
(SEQ ID NO: 9)
5'GAGGTTCAGCTGCAGCAGTCTGGGGCAGAGTTTGTGA(G/A)GCCAGG GGCCTCAGTCAAGTTGTCCTGCAGAGTTTC<u>TGGCTTCAACATTAAGGACT ACTAT</u>ATTAACTGGGTGAAGCAGAGGACTGAACAGGGCCTGGAGTGGATT GGAAGG<u>ATTGATCCTGAGGATGGTGAAACT</u>AAATATGCCCCGAAATTCCA

GGGCAAGGCCACTATAACAGCAGACACATCCTCCAACACAGCCAACCTGC

ACCTCAGCAGCCTGACATCTGCGGACACTGCCGTCTATTACTGT<u>GCTAGC

TCAGGCTACGCCTTTGCCTGGTTTCTTTAC</u>TGGGGTCAGGGGACTCTGGT

CACTGTCTCTGCA-3'

2G7Variable Light:
(SEQ ID NO: 10)
5'CAAAATGTTCTCACCCAGTCTCCAGCAATCATGTCTGCATCTCCAGGG GAGAAGGTCACCATGACCTGCAGTGCCAGC<u>TCAAGTGTAAGTTAC</u>ATGCA CTGGTACCAGCAGAAGTCAGGCACCTCCCCCAAAAGATGGATTTAT<u>GACA CATCC</u>AAACTGGCTTCTGGAGTCCCTGCTCGCTTCAGTGGCAGTGGGTCT

GGGACCTCTTATTCTCTCACAATCAGCAGCATGGAGGCTGAAGATGCTGC

CACTTATTACTGC<u>CAGCAGTGGAGTAGTAACCCGCTCACG</u>TTCGGTGCTG

GGACCAAGCTGGAGCTGAAACGT-3'

-continued

2G7Variable Heavy:
(SEQ ID NO: 11)
5'GAGGTTCAGCTGCAGCAGTCTGGGGCAGAGCTTGTGAAGCCAGGGGCC

TCAGTCAAGTTGTCCTGCACAGCTTCTGGCTTCAACATTAAAGACTACTT

TATACACTGGGTGAACCAGAGGACTAAACAGGGCCTGGAGTGGATTGGAA

GGATTGATCCTGAGGATGGTGAAACTAAATATGCCCCGAAATTCCAGGGC

AAGGCCACTTTAACAGCAGACACAACCTCCAACACAGCCGACCTTCAGCT

CAGCAGTCTGACATCTGAGGACACTGCCGTCTATTACTGCGTTCTTTACT

ACAGTCGAAGCTTTGACTACTGGGGCCAAGGCACCACTCTCACAGTCTCC

TCA-3'

3B12Variable Light:
(SEQ ID NO: 12)
5'GACATCTTGCTGACTCAGTCTCCAGCCATCCTGTCTGTGAGTCCAGGA

GAAAGAGTCAGTTTCTCCTGCAGGGCCAGTCAGAGCATTGGCACAAGCAT

ACACTGGTATCAGCAAAGAACAAATGGTTCTCCAAGGCTTCTCATAAAGT

ATGCTTCTGAGTCTATCTCTGGGATCCCTTCCAGGTTTAGTGGCAGTGGA

TCAGGGACAGATTTTACTCTTAGCATCAATAGTGTGGAGTCTGAAGATAT

TGCAGATTATTACTGTCAACAAAGTAATAGATGGCCATTCACGTTCGGCT

CGGGGACAAAGTTGGAAATAAAACGT-3'

3B12Variable Heavy:
(SEQ ID NO: 13)
5'GAGGTTCAGCTGCAGCAGTCTGGGGCAGAGTTTGTGAAGCCAGGGGCC

TCAGTCAAGTTGTCCTGCAGAGTTTCTGGCTTCAACATTAAGGACTACTA

TATTAACTGGGTGAAGCAGAGGACTGAACAGGGCCTGGAGTGGATTGGAA

GGATTGATCCTGAGGATGGTGAAACTAAATATGCCCCGAAATTCCAGGGC

AAGGCCACTATAACAGCAGACACATCCTCCAACACAGCCAACCTGCACCT

CAGCAGCCTGACATCTGCGGACACTGCCGTCTATTACTGTGCTAGCTCAG

GCTACGCCTTTGCCTGGTTTCTTTACTGGGGTCAAGGGACTCTGGTCACT

GTCTCTGCA-3'

Also provided is a cell that includes (e.g., expresses) a polynucleotide as disclosed above. For example, the cell may comprise a polynucleotide that encodes SEQ ID NO:2 and/or 3, a polynucleotide that encodes SEQ ID NO: 4 and/or 5, a polynucleotide that encodes SEQ ID NO:6 and/or 7, or a polynucleotide that encode one or more or all of the complementarity determining regions of SEQ ID NO: 2, 3, 4, 5, 6 and 7 (listed in Table 1) or combinations thereof. The cell may be a monoclonal-antibody producing hybridoma, or an isolated B-cell. In certain embodiments, the cell is a sensor cell as described herein useful in connection with the BIOFLASH™ detection format. The sensor cell may express at least one antibody of the invention on its extracellular surface.

Methods, Systems, and Detection Formats

The antibodies and fragments described herein can be used in methods for detecting PBP2a or methicillin-resistant *Staphylococcus* (or MRSA) in a sample. The sample may be any sample suspected of containing MRSA, including, for example, a sample obtained from an patient or subject, or from an environmental site. Examples of biological samples include body fluids and tissue specimens that are infected, and/or which are suspected of containing *S aureus* or MRSA. The source of the sample may be physiological medium such as blood, serum, wound drain, CSF, sputum, plasma, breast milk, pus, tissue scrapings, washings, urine, feces, tissue, such as lymph nodes, spleen or the like. The sample may be a sample derived from a wound, burn, or ulcer, for example, by testing drainage, irrigant, or swab from the region.

Methods for the detection of PBP2a or methicillin-resistant *Staphylococcus* in a sample include contacting the sample with an antibody or antibody fragment as described herein. Subsequently the binding of the antibody to the PBP2a antigen, if present, can be detected. Binding of the antibody or antibody fragment to the antigen will indicate the presence of PBP2a, and by association, methicillin-resistant *staphylococcus* or MRSA. Binding of the antibody or antibody fragment can be indicated by various mechanisms, such as a color change or luminescence.

The methods of the invention may employ antibodies that recognize PBP2a, with little cross-reactivity or signal from Protein A binding, or other epitopes of *S. aureas* that are not associated with MRSA. Thus, the invention provides methods that selectively recognize MRSA in samples over other non-MRSA *Staphylococcus* that may be present.

The method of the invention in some embodiments comprise contacting the sample with antibodies against Protein A, to detect the presence of *Staphylococcus aureus* in the sample. In such embodiments, the presence of Protein A and PBP2a on bacterial cells is indicative of the presence of MRSA. For example, using an ELISA or lateral flow strip assay as described elsewhere herein, a first antibody may be directed against PBP2a (and may be an antibody of the invention), and a second antibody may be directed against Protein A. The first antibody or the second antibody may be immobilized. In accordance with these embodiments, the invention detects cells or cellular debris having both the PBP2a and Protein A markers, thereby being indicative of the presence of MRSA.

Alternatively, *Staphylococcus aureus* bacteria in a sample may be captured, isolated, or immobilized via the presence of Protein A on their surface. Antibodies against Protein A may be used for this purpose. The captured, isolated, or immobilized material may be used for the detection of PBP2a on methicillin-resistant cells, to thereby indicate the presence of MRSA. For example, immobilized antibodies against Protein A may be used to capture and remove *Staphylococcus aureus* from a sample, followed by testing of the captured material for the presence of PBP2a as described herein. Alternatively, cells expressing PBP2a may be captured or immobilized, with this material used to detect the presence of Protein A.

The method may employ a detection reagent system. The detection reagent system may comprise an antibody of the invention or as described herein, a detectable label, and/or reagents necessary to perform the binding and detectable reactions. Detectable labels include reagents with directly detectable elements (e.g., radiolabels) and reagents with indirectly detectable elements (e.g., a reaction product). Examples of detectable labels include radioisotopes, bioluminescent compounds, chemiluminescent compounds, fluorescent compounds, metal chelates, and enzymes. A detectable label can be incorporated into a binding moiety by chemical or recombinant methods to form a detection reagent system. A detectable label with an indirectly detectable element includes an enzyme that will react with a substrate to produce a detectable signal, i.e., the presence of the enzyme used as a label is not directly measured. The detection system may be an ELISA assay or a lateral-flow chromatographic strip assay.

Detectable labels can be coupled to an antibody or an antibody fragment of the invention through a chemical linker. Linkers can be polypeptide sequences, such as poly-Glycine sequences of between about 5 and 200 amino acids. Proline residues can be incorporated into a polypeptide linker to prevent the formation of significant secondary structural elements, i.e., α-helix/β-sheet, by the linker. An example of a flexible linker is a polypeptide that includes a glycine chain with an intermediate proline. In other examples, a chemical linker is used to connect synthetically or recombinantly produced binding and labeling domain subsequences. Such flexible linkers are known to persons of skill in the art. For example, poly(ethylene glycol) linkers are available from Shearwater Polymers, Inc. Huntsville, Ala. These linkers optionally have amide linkages, sulfhydryl linkages, or heterofunctional linkages.

The detectable labels used in the methods described herein, which are attached to or associated with binding moieties in the detection reagent system, can be primary labels (where the label comprises an element that is directly detectable or that produces a directly detectable element) or secondary labels (where the detectable label binds to another element to produce a detectable signal, e.g., as is common in immunological labeling using secondary and tertiary antibodies). Various primary and secondary labels and their uses are described in U.S. Pat. Nos. 3,817,837; 3,850,752; 3,939,350; 3,996,345; 4,277,437; 4,275,149; and 4,366,241, which are hereby incorporated by reference. Secondary and tertiary antibodies can be used to amplify detection levels.

Primary and secondary labels include undetected elements as well as detected elements. Useful primary and secondary labels in the methods described herein include spectral labels such as green fluorescent protein, fluorescent dyes (e.g., fluorescein and derivatives such as fluorescein isothiocyanate (FITC) and Oregon Green™, rhodamine and derivatives (e.g., Texas red and tetrarhodimine isothiocynate (TRITC)), biotin, phycoerythrin, AMCA, and CyDyes™), radiolabels (e.g., $^3$H, $^{125}$I, $^{35}$S, $^{14}$C, $^{32}$P, and $^{33}$P), enzymes (e.g., horseradish peroxidase and alkaline phosphatase), spectral colorimetric labels such as colloidal gold or colored glass or plastic (e.g., polystyrene, polypropylene, and latex) beads. As a wide variety of labels can be used, the choice of a label depends on factors such as the sensitivity required, the ease of conjugation with the binding moiety, the stability of the label or system, the available instrumentation, and the disposability of the assay components, e.g., radiolabels. Further examples of labels include those that use (1) chemiluminescence (e.g., horseradish peroxidase and/or alkaline phosphatase with substrates that produce photons as breakdown products (kits available from Molecular Probes, Amersham, Boehringer-Mannheim, and Life Technologies/Gibco BRL)); (2) color production (horseradish peroxidase and/or alkaline phosphatase with substrates that produce a colored product) (kits available from Life Technologies/Gibco BRL and Boehringer-Mannheim)); and (3) fluorescence (an enzyme such as alkaline phosphatase, together with the substrate, such as AttoPhos (Amersham), that produce fluorescent products). Other methods for labeling and detection will be readily apparent to those skilled in the art.

The presence or absence, or amount, of a label can be detected by visual inspection by an operator or by a detector designed to monitor a particular detector reagent system. Examples of typical detectors include spectrophotometers, phototubes/photodiodes, microscopes, scintillation counters, cameras, and film, as well as combinations thereof. Suitable detectors are widely available from a variety of commercial sources known to persons of skill in the art. The detection system may be qualitative, quantitative, or semi-quantitative.

The detection of PBP2a/MRSA can be carried out using methods involving a wide variety of assay formats. For example, the assay format may involve immobilization of a binding reagent system on a solid support, followed by exposure of the sample and the detection of any binding to the binding reagent system.

In certain embodiments, the assay system is based on the enzyme-linked immunosorbent assay (ELISA) method. General methods for ELISA are well known to those of skill in the art (see, e.g., Elder et al. (1982) *J. Clin. Microbiol.* 16:141; Current Protocols in Molecular Biology, F. M. Ausubel et al., eds., Current Protocols, Greene Publishing Associates, Inc. and John Wiley & Sons, Inc. (1995 Supplement) (Ausubel et al.)). In general, antigens are fixed to a solid surface and are detected using antigen-specific antibodies by way of an enzymatic reaction. The ELISA method can also be used in a "sandwich" mode wherein the antigens are bound to the solid surface via antibodies or antibody binding fragments described herein that are bound to the solid surface. A second antibody, typically linked to an enzyme, is then contacted to the antigen, washed, then contacted with the enzyme substrate to select binding. These and other ELISA method are taught in, for example, Ausubel et al. §11.2.

To immobilize antibodies or antibody fragments as described herein to a solid support, a capture reagent may be employed that is non-diffusively associated with the support. The capture reagents can be non-diffusively immobilized on the support either by covalent or non-covalent methods, which are known to those of skill in the art. See, e.g., Pluskal et al. (1986) *BioTechniques* 4: 272-283. Examples of supports include, but are not limited to, glass, plastics, polymers, membranes (chromatographic membranes or filters) metals, metalloids, ceramics, and organic surfaces. Further examples include, but are not limited to, microtiter plates, nitrocellulose membranes, nylon membranes, and derivatized nylon membranes, beads, and also particles, such as agarose and SEPHADEX™ (GE Healthcare Bio-Sciences AB, Ltd.; Uppsala, Sweden). When the solid support is a membrane, the test sample can flow through the membrane, for example, by gravity, capillary action, or under positive or negative pressure. Assay systems for use in the methods and kits described herein include, but are not limited to, dipstick-type devices, immuno-chromatographic test strips, radial partition immunoassay devices, microtiter assays, and flow-through devices.

Once a test sample has been contacted with such a solid support, the solid support is then contacted with the binding antibodies or antibody fragments of the invention as described herein. Optionally, the solid support can be washed prior to contact with detection reagents to remove unbound reagents and test sample components. After incubation of the detection reagents for a sufficient time to bind to a substantial portion of the immobilized antigen(s), any unbound labeled reagents are removed, for example, by washing. The detectable labels are then detected. For example, in the case of an enzyme used as a detectable label, a substrate for the enzyme that turns a visible color upon action of the enzyme is placed in contact with the bound detection reagent. A visible color is generated in proportion to the amount of antigen(s) in the sample (e.g. PBP2a or Protein A).

Further examples of assay methods include membrane-based detection systems such as those described in U.S. Pat. No. 5,922,615, which is hereby incorporated by reference. These membrane-based detection systems employ an apparatus that includes a porous member, e.g., a membrane or a filter, onto which is bound a multiplicity of capture reagents such as the antibodies and antibody fragments disclosed herein.

Competitive binding assays can also be used to detect PBP2a antigen, or MRSA. Competitive binding assays are performed using the described devices by adding to a sample a labeled analog of PBP2a antigen or competing epitope thereof. The labeled analog of PBP2a antigen and any unlabeled polypeptides containing PBP2a antigen present in the sample compete for the binding sites of the capture reagents, i.e., the antibodies or antibody fragments described herein. Alternatively, the capture reagents can be combined with the sample and labeled analogs with subsequent immobilization of the capture reagents onto a porous member. An additional fluid can be added to separate the free from bound label, followed, if needed, by a signal development solution to enable detection of the label of the labeled analog that has interacted with the capture reagent immobilized on the porous member. The amount of labeled PBP2a antigen that is bound to the porous member is related to the amount of PBP2a antigen in the sample.

Samples existing as a bioaerosol or capable of forming a bioaresol can also be analyzed. An example of a bioaerosol detector is a self-contained biosensor containing calcium sensitive bioluminescent molecules and surface-bound antibodies of antibody fragments. Recognition of minute amounts of a specific pathogen by the surface-bound antibodies creates elevated levels of intracellular calcium. The elevated levels of calcium cause the calcium sensitive bioluminescent molecules to luminesce. Such luminescence, which is a direct indication of the presence of the pathogen being monitored, is then detected and optionally quantified by a light meter, such as a luminometer. Example of this type of bioaerosol detector are described in U.S. Pat. Nos. 6,087,114, 6,248,542, and 7,214,346, which are incorporated herein in their entirety, and particularly with respect to the biosensor system described therein.

For example, a sample suspected of containing Penicillin Binding Protein 2a (PBP2a) antigen or *S. aureus*, or MRSA, may be contacted with a sensor cell expressing on the sensor cell surface a Penicillin Binding Protein 2a (PBP2a) antibody or antibody fragment of the invention as described herein. The sample may be pre-processed in some embodiments to concentrate or isolate the antigenic components. The binding of the sensor cell with its cognate antigen can be detected to indicate the presence of methicillin-resistant *Staphylococcus aureus* in the sample.

Microbial cells, or an isolated population of microbial cells, which may be *Staphylococcus aureus*, are contacted with a sensor cell expressing a Penicillin Binding Protein 2a (PBP2a) antibody or antibody fragment as described herein. The *Staphylococcus aureus* component of the sample may be isolated or partially purified as described above (via Protein A on their surface), to remove other potentially methicillin-resistant microbes from the sample, such as MRSE.

The microbial cells in the sample may be lysed prior to contacting the sensor cell. For example, a conventional step of gram positive cell lysis can be used to release the intracellular components. Any enzyme that could lyse a cell in order to release the cellular components could be used. The lysis process can be an enzymatic process or non-enzymatic process, e.g. heat shock, osmotic shock, sonication.

The binding of the sensor cell with the PBP2a antigen can be detected to indicate the presence of methicillin-resistant *Staphylococcus aureus* in the sample. Sensor cells and methods and devices for using the same are described in U.S. Pat. Nos. 6,087,114 and 6,248,542, which are incorporated herein in their entirety.

Sensor cells include biomarker cells for use with the BIOFLASH® system based on the CANARY® (Cellular Analysis and Notification of Antigen Risks and Yields) technology (Innovative Biosensors, Inc., Rockville, Md.). BIOFLASH® can be used to rapidly detect the presence of PBP2a antigen by detecting the binding of the PBP2a antigen with a sensor cell comprising a PBP2a antibody or fragment.

The BIOFLASH® system can comprise one or more sensor cells comprising an engineered biosensor expressing membrane bound PBP2a-specific antibodies (as described) and a calcium sensitive bioluminescent molecule. Binding of the antibodies by PBP2a antigen leads to elevation of intracellular calcium and light emission. The amplified light output can be detected by, for example, using a luminometer. When the PBP2a antigen to be detected binds to the antibodies on the surface of a sensor cell, calcium ions move into the cytosol as described in Wilson et al., J Exp Med 166:601-606 (1987). The increased cytosolic calcium concentration causes an emitter molecule to emit a photon, which can be read by the optical detector.

A suitable emitter molecule is any molecule that will emit a photon in response to elevated cytosolic calcium concentrations, including bioluminescent and fluorescent molecules. One emitter molecule, the bioluminescent aequorin protein, is described in Button et al., Cell Calcium 14:663-671 (1993); Shimomura et al., Cell Calcium 14:373-378 (1993); and Shimomura, Nature 227:1356-1357 (1970). Aequorin generates photons by oxidizing coelenterazine, a small chemical molecule. Coelenterazine diffuses through cellular membranes, so coelenterazine or an analog thereof can be added to the culture medium surrounding the cells. Alternatively, genes encoding enzymes that make coelenterazine can be introduced into the cells. Optionally, bioluminescent green fluorescent protein (GFP) can be used (see Chalfie, Photochem Photobiol 62:651-656 [1995]). Using GFP, the cell cytosol contains both GFP and aequorin. In response to elevated calcium in the cytosol, aequorin donates energy to GFP in an emissionless energy transfer process. GFP then emits the photon. Alternatively, the emitter molecule can be a calcium-sensitive fluorescent molecule (e.g., indo-1) which is illuminated by a wavelength of light suitable to induce fluorescence.

Aequorin, or any other emitter molecule, can be introduced into the cell by methods well know in the art. If the emitter molecule is a protein (as is the case with aequorin), the cell can contain an expression vector encoding the protein (i.e., a nucleic acid or virus which will produce the emitter molecule when introduced into a cell). An expression vector can exist extrachromosomally or integrated into the cell genome.

A sensor cell with surface-bound antibodies or fragments can be either prokaryotic or eukaryotic. Upon binding of PBP2a antigen to the antibodies, the cell mobilizes calcium ions into the cytosol. An example of a sensor cell is a B cell (i.e., a B cell from a cold or warm-blooded vertebrate having a bony jaw) which can be genetically engineered to express one or more surface-bound monoclonal antibodies. The B cells are optionally genetically engineered to express a calcium sensitive bioluminescent cytosolic molecule.

Another useful cell type that can be used is a fibroblast that optionally can be adhered to a substrate or device. However, fibroblasts do not contain the signal transduction machinery to transfer a signal from the cytoplasmic portion of a surface antibody to calcium stores in the cell. To overcome this problem, a chimeric surface antibody can be expressed in the fibroblast. This chimeric antibody contains a cytoplasmic amino acid sequence derived from a polypeptide (e.g., a fibroblast growth factor receptor) that can transduce a signal from the inner surface of the plasma membrane of the fibroblast to intracellular calcium stores. Thus, when an antigen binds to the extracellular portion of the chimeric antibody to cause antibody aggregation on the surface, calcium mobilization is induced. A similar strategy using chimeric antibodies can be employed for any other non B-cell type. The fibroblast can also be optionally genetically engineered to express a calcium sensitive bioluminescent cytosolic molecule.

Growth of the cell or cells can be controlled by any means well known in the art, including providing anti-mitotic drugs (e.g., α-amanitin) or growth factors (e.g., fetal bovine serum) in the medium. Cells can also be genetically engineered to grow at a determined rate. As discussed above, cells can be used where binding of the PBP2a antigen to the antibodies on the surface of the cell leads to an increase in calcium concentration in the cytosol. In fact, the cell can be a non-living, manufactured unit as long as it satisfies the above factors.

Optionally, one or more lysed samples are contacted with an antibody or antibody fragment that binds with a PBP2a antigen prior to contacting the sensor cell, which also comprises a PBP2a antibody or antibody fragment as described above. The lysis process can be carried out concurrently with this pre-sensor cell PBP2a binding process. The pre-sensor cell PBP2a binding process can be used to capture solubilized PBP2a released from lysed S. aureus cells. Optionally, a resulting sample comprising captured solubilized PBP2a can be centrifuged to decrease the sample volume for the sensor cells.

Antibodies that bind to desired antigens and methods of making the same are known in the art. For example, Protein A is commercially available from AbCam (Cambridge, Mass.) and other commercial sources. PBP2a antibodies and methods for making the same have also been reported. For example, Ohwada et al., DNA Vaccination by mecA Sequence Evokes an Antibacterial Immune Response Against Methicillin-resistant *Staphylococcus aureus*, J. Antimicrob. Chemother. (1999) 44(6): 767-74, describes production of PBP2a antibodies by injection of a mecA-expressing plasmid into BALB/c mice. Anti-PBP2a antibody was detected in the sera obtained from the DNA-vaccinated mice.

The antibodies or antibody fragments of the invention may be provided in the form of a kit. The kit can comprise a plurality of containers, each containing an binding agent of the invention in solution or lyophilized form. At least one antibody in the kit is labeled for detection. The kit may further comprise an antibody for binding Protein A, where the combined detection of Protein A and PBP2a is indicative of MRSA as described herein. Such a kit can also contain components necessary to perform the assays described above, such as ELISA or lateral flow strip assay, or other assays. For example, the kit can include sensor cells such as those described herein. These kits can further include an apparatus for collecting, storing, and/or disposing of a sample. Kits as described can include instructions, for example, for performing an assay or preparing a sample. Such kits can contain each apparatus and chemical needed to perform an assay or contain only certain elements of an assay.

Methods for Reducing or Preventing MRSA Infection

Further provided is a method of reducing or preventing *S. aureus* or MRSA infection, or for enhancing the effectiveness of a beta-lactam antibiotic, in a subject. The method generally comprises administering to the subject an effective amount of an antibody or antibody composition disclosed herein. An effective amount of a compound is sufficient to provide the desired result (i.e., passive immunity, or blocking of PBP2a), usually without substantial toxicity. As will be pointed out below, the exact amount required will vary from subject to subject, depending on the species, age, and general condition of the subject, the severity of the infection that is being treated, the particular compound used, its mode of administration, and the like. Thus, it is not possible to specify an exact effective amount. However, an appropriate effective amount can be determined by one of ordinary skill in the art.

A subject is an individual. A subject includes is generally a mammal, such as a human, horse, pig, rabbit, dog, sheep, goat, non-human primate, cow, cat, guinea pig or rodent. The term does not denote a particular age or sex. A patient refers to a subject with a disease or disorder or suspected of having a disease or disorder. The term patient includes human and veterinary subjects.

The antibody of the invention may be formulated or co-administered with a β lactam antibiotic, such as penicillin.

The dosages or amounts of the compositions described herein are large enough to produce the desired effect (i.e., passive immunity) in the method by which delivery occurs. The dosage should not be so large as to cause adverse side effects, such as unwanted cross-reactions, anaphylactic reactions, and the like. Generally, the dosage will vary with the age, condition, sex and extent of the infection in the subject and can be determined by one of skill in the art. The dosage can be adjusted by the individual physician based on the clinical condition of the subject involved. The dose, schedule of doses and route of administration can be varied.

The efficacy of administration of a particular dose of the compounds or compositions according to the methods described herein can be determined by evaluating the particular aspects of the medical history, signs, symptoms, and objective laboratory tests that are known to be useful in evaluating the status of a subject with an infection or at risk for infection. These signs, symptoms, and objective laboratory tests will vary, depending upon the nature and extent of the infection being treated or prevented, as will be known to any clinician who treats such patients or a researcher conducting experimentation in this field. For example, if, based on a comparison with an appropriate control group and/or knowledge of the normal progression of the infection in the general population or the particular individual: 1) a subject's physical condition is shown to be improved, 2) the progression of the infection is shown to be stabilized, slowed, or reversed, or 3) the need for other medications for treating the infection is lessened or obviated, then a particular treatment regimen will be considered efficacious. For example, reducing or preventing infection in a subject or in a population would indicate efficacy. Such effects could be determined in a single subject (e.g., by reducing the number of bacteria detected with a biological sample) or in a population (e.g., using epidemiological studies).

The antibodies or fragments and pharmaceutical compositions described herein can be administered to the subject in a number of ways depending on whether local or systemic treatment is desired, and on the area to be treated. Thus, for example, a compound or pharmaceutical composition described herein can be administered intravenously, subcutaneously, intramuscularly, encapsulated in liposomes or microspheres, as an ophthalmic solution and/or ointment to the surface of the eye, as a nasal spray, as a nebulized solution, or as an aerosol to the nasal cavities or airways. Moreover, a compound or pharmaceutical composition can be administered to a subject vaginally, rectally, intranasally, orally, by inhalation, orally, or by intubation. Optionally, the composition can be administered by intravenous, subcutaneous, intramuscular, or intraperitoneal injection. The composition can be prepared in conventional forms, either as liquid solutions or suspensions, solid forms suitable for solution or suspension in liquid, or as emulsions. Optionally, administration can be by slow release or sustained release system such that a constant dosage is maintained. See, e.g., U.S. Pat. No. 3,610,795, which is incorporated by reference herein for the methods taught therein.

The compositions taught herein include sterile aqueous or non-aqueous solutions, suspensions, and emulsions which can also contain buffers, diluents and other suitable additives. Examples of non-aqueous solvents are propylene glycol, polyethylene glycol, vegetable oils such as olive oil, and organic esters such as ethyl oleate. Aqueous carriers include water, alcoholic/aqueous solutions, emulsions or suspensions, including saline and buffered media. Vehicles include sodium chloride solution, Ringer's dextrose, dextrose and sodium chloride, lactated Ringer's, or fixed oils. Preservatives and other additives can also be present such as, for example, antimicrobials, anti-oxidants, chelating agents, and inert gases and the like.

Formulations for local administration can include ointments, lotions, creams, gels, drops, suppositories, sprays, liquids, aerosols, nebulizer solutions and powders. Conventional pharmaceutical carriers, aqueous, powder or oily bases, thickeners and the like can be necessary or desirable.

Compositions for oral administration can include powders or granules, suspensions or solutions in water or non-aqueous media, capsules, sachets, or tablets. Thickeners, flavorings, diluents, emulsifiers, dispersing aids or binders can be desirable.

Provided herein are pharmaceutical compositions comprising the antibodies or fragments thereof disclosed herein. The composition further comprises a pharmaceutical carrier. Such compositions are useful in developing passive immunity to *S. aureus* or MRSA. Optionally, the composition is suitable for administration to a mucosal surface, but other routes of administration are disclosed, including systemic administration as described herein.

Antibody or antibody fragments described herein can be linked to a therapeutic agent, thereby forming a molecular complex. For example, the complex could be designed to target PBP2a positive cells and cause a desired physiologic effect including, for example, cell death or stasis. The linkage can be covalent, but can also be noncovalent (e.g., ionic). Therapeutic agents include but are not limited to toxins, including but not limited to plant and bacterial toxins, small molecules, peptides, polypeptides and proteins. Genetically engineered fusion proteins, in which genes encoding an antibody or fragment(s) thereof, including the Fv region, can be fused to the genes encoding a toxin to deliver a toxin to the target cell are also provided. Other examples of therapeutic agents include adjuvants, antibacterial agents, chemotherapeutic agents, a radiotherapeutic agent, and immunotherapeutic agent, as well as combinations thereof.

The therapeutic agent can act extracellularly, for example by initiating or affecting an immune response, or it can act intracellularly, either directly by translocating through the cell membrane or indirectly by, for example, affecting transmembrane cell signaling. The therapeutic agent is optionally cleavable from the antibody or fragment. Cleavage can be autolytic, accomplished by proteolysis, or affected by contacting the cell with a cleavage agent. Moreover, the antibody or fragments thereof can also act extracellularly, for example by initiating, affecting, enhancing or reducing an immune response without being linked in a molecular complex with a therapeutic agent.

Techniques for conjugating a therapeutic moiety to antibodies are well known, see, e.g., Amon et al., Monoclonal Antibodies For Immunotargeting Of Drugs In Cancer Therapy, in Monoclonal Antibodies And Cancer Therapy, Reisfeld et al. (eds.), pp. 243-56 (Alan R. Liss, Inc. 1985); Hellstrom et al., Antibodies For Drug Delivery, in Controlled Drug Delivery (2nd Ed.), Robinson et al. (eds.), pp. 623-53 (Marcel Dekker, Inc. 1987); Thorpe, Antibody Carriers Of Cytotoxic Agents In Cancer Therapy: A Review, in Monoclonal Antibodies '84: Biological And Clinical Applications, Pinchera et al. (eds.), pp. 475-506 (1985); Analysis, Results, And Future Prospective Of The Therapeutic Use Of Radiolabeled Antibody In Cancer Therapy, in Monoclonal Antibodies For Cancer Detection And Therapy, Baldwin et al. (eds.), pp. 303-16 (Academic Press 1985), and Thorpe et al., The Preparation And Cytotoxic Properties Of Antibody-Toxin Conjugates, Immunol. Rev., 62:119-58 (1982). Alternatively, an antibody can be conjugated to a second antibody to form an antibody heteroconjugate as described by Segal in U.S. Pat. No. 4,676,980.

The antibodies or fragments thereof can also be administered in combination with effective amounts of one or more other therapeutic agents. The antibodies or fragments thereof can be administered sequentially or concurrently with the one or more other therapeutic agents. The amount of antibody or fragment thereof and therapeutic agent can depend, for example, on what type of therapeutic agents are used, the condition being treated, and the scheduling and routes of administration but would generally be less than if each were used individually.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the scope except as and to the extent that they are included in the accompanying claims. Efforts have been made to ensure accuracy with respect to numbers (e.g., amounts, temperature, etc.), but some errors and deviations should be accounted for.

Example 1

Antibody Raised Against a Peptide Containing SEQ ID NO:1

An antibody raised against a peptide containing SEQ ID NO:1 was developed and used to create a sensor cell line using the CANARY® platform technology (Innovative Biosensors, Inc.; College Park, Md.). The CANARY® platform sensor cell line was developed by cloning the raised antibody heavy and light chain variable regions into a shuttle vector system and transfecting the genes into a parental B cell line that expresses a bioluminescent gene (CANARY® platform) (as described in Rider et al. (2003) *Science* 301:213-215, which is incorporated herein by reference in its entirety, at least for methods and compositions taught therein). The antibodies were developed such that they would localize to a cell surface and were therefore available for binding to their intended target, in this case a PBP2a domain. Binding events for the developed antibodies result in mobilization of intracellular calcium and activation of the bioluminescent response of the CANARY® platform sensor cells.

Of the populations of CANARY® platform cells thus generated, cells that stably expressed the antibody constructs in addition to the bioluminescent gene were selected. Exposure of the selected CANARY® platform cells to a solution that contained a target PBP2a protein resulted in a luminescent response that was measured using a single-tube benchtop luminometer (FIG. 1). In FIG. 1, the curves represent luminometer readings for samples containing polystyrene beads coated with PBP2a (beads with target) or uncoated (beads without target) that were exposed to the engineered B cells. As shown in FIG. 1, the luminescent response of the selected CANARY® B cells was 250-fold higher in the presence of PBP2a than in the absence of PBP2a. This increase in luminosity demonstrated that the engineered CANARY® B cells responded to the presence of the PBP2a target.

Example 2

B-Cell Line Development

Supernatants from selected hybridomas were analyzed for antibody (Ab)-antigen affinity using BIACORE™ analysis (Biacore, Inc., Piscataway, N.J.). The antibody Kd was determined by coating the antigen-rPBP2a on a BIACORE™ CM5 chip (Biacore, Inc., Piscataway, N.J.), and the binding assay was performed by flowing the antibody over the antigen. This method provided the binding affinity and the avidity depending on the density of the antigen used to coat the chip.

The CM5 chip which has carboxymethyl dextran on the surface was used for coupling the antigen-rPBP2a. Prior to coupling, the chip surface was activated with 1-ethyl-3(3-dimethylaminopropyl)carbodiimide (EDC) and N-hydroxysuccinimide (NHS).

The rPBP2a was used at a concentration for 5 μg/ml in 10 mM NaAcetate buffer, pH4.5 to coat the chip at a flow rate of 5 μL/min. The pH of 4.5 was found to be the best in comparison with pH 5.0 and pH 5.5. To determine the kinetics, 0 to 5 nM concentration of antibody was tested at a flow rate of 20 μL/min. The antibody dilutions were made in a buffer containing 10 mM HEPES (pH 7.4), 150 mM NaCl, 3 mM EDTA, 0.005% P20 (polyoxyethylenesorbitan). For each antibody the Kd was determined on several occasions and with several preparations.

The chip was regenerated in between different antibody treatments with 10 mM Glycine (pH 1.75).

BIACORE™ (Biacore, Inc., Piscataway, N.J.) determination of Kd (M) for PBP2a antitbodies.

| Antibody | Culture Sup 1 | Culture Sup 2 | Purified Antibody |
|---|---|---|---|
| 2G7 | $2.04 \times 10^{-13}$ | $2.2 \times 10^{-15}$ | $1.18 \times 10^{-12}$ |
| 3B12 | $4.85 \times 10^{-9}$ | $6.05 \times 10^{-9}$ | $1.76 \times 10^{-10}$ |
| 2B2 |  | $2.15 \times 10^{-9}$ | $3.59 \times 10^{-10}$ |

The results demonstrated high reproducibility between several preparations and several days of testing. The Kd of clone 2G7 was in the range of $10^{-12}$ to $10^{-15}$ M, which approaches the Kd of biotin-avidin interaction.

Example 3

Unique Epitope Mapping of Antibodies

For epitope mapping, on to the same rPBP2a Biacore CM5 chip, higher concentration (500 nM) of a given antibody was used to saturate the binding site, and then the second antibody was injected to see if there was another binding event. The flow rate of antibody used for epitope mapping was 20 μL/min.

Each antibody was injected multiple times until it did not result in an increase in relative signal units to make sure that all epitopes were bound by that antibody. Following this, a second antibody was contacted and, if this antibody recognized a unique epitope, it resulted in an increase in relative signal units. However, if the epitope for this antibody was already saturated by a previous antibody, then an increase in relative signal units was not observed.

Figure 2:
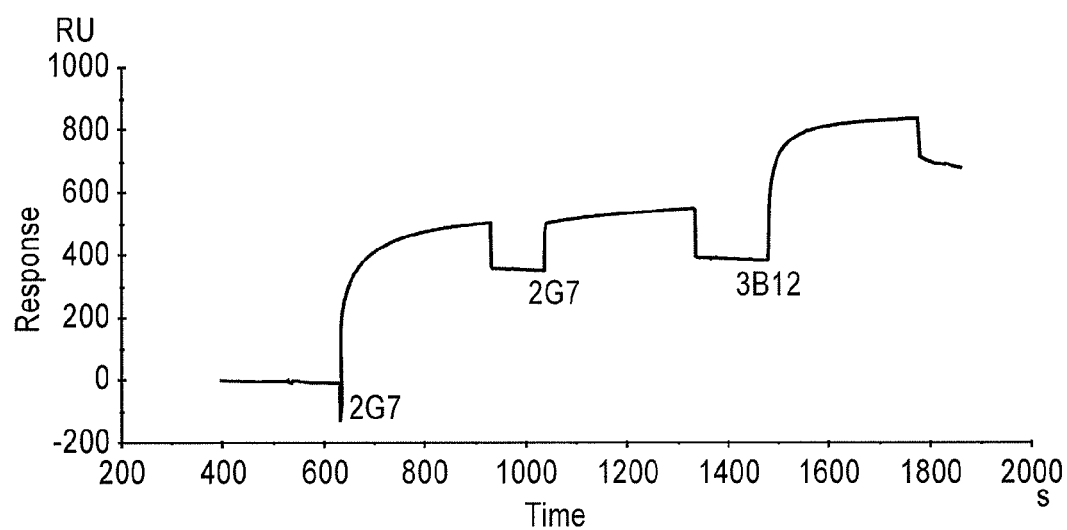
FIG. 2 shows epitope mapping of antibodies by exposing a PBP2a coated chip with 2G7 antibody and subsequently contacting the chip with 3B12 antibody.

Epitope mapping was performed for the 2B2, 3B12 and 2G7 antibodies. As shown in FIG. 2, exposure of the PBP2a coated chip to 2G7 antibody resulted in increase in signal. Subsequent treatment with 3B12 resulted in additional increase in relative signal units indicating that they both bind to unique epitopes. Similarly subsequent treatment with 2B2 also increased signal units. This data indicated that each of the three antibodies bind to distinct binding domains. For the CANARY® (Innovative Biosensors, Inc., Rockville Md.) assay this indicated that using 2G7 B cells either 3B12 or 2B2 can be used as capture antibodies, similarly using 3B12 B cells 2G7 and 2B2 can be used as capture antibodies, and using 2B2 B cells 2G7 and B12 can be used as capture antibodies.

Example 4

Western Analysis with Monoclonal Antibodies

Prototype MRSA strain BAA43 and MSSA starin 12593 were cultured on plates. A suspension of bacteria in PBS to equal an $OD_{595\,nm}$ of approximately 1 was prepared in a total volume of 11 mL and 10 mL was processed. Following centrifugation the total bacterial pellet was suspended in 1.5 mL of 1 TE buffer (10 mM Tris-HCl (pH 7.5), 1 mM EDTA). 145,000 units (5 μl) of READY-LYSE® Lysozyme (Epicentre, Madison, Wis., #R1810M, $10^6$ U @ 29,000 U/μl) and 20 units in 2 μL of lysostaphin (Sigma, Wilmington, Del., # L4402 at 5 mg/ml dissolved in $diH_2O$, specific activity ~2000 U/mg protein) was added to this and incubated in 37° C. water bath for 30 minutes to 1 hour, until the solution cleared. The digest was centrifuged at 15,000×g for 15 minutes to pellet unlysed bacteria and DNA. The supernatant was transferred to a CENTRICON® YM-50 ((Millipore, Billerica, Mass.) (Fisher, Pittsburgh, Pa., product #4225) filter unit pepared by pre-rinsing with 1 ml of $diH_2O$ at 5000×g for 5 minutes. The bacterial supernatant was transferred into the CENTRICON® unit and centrifuged at 5000×g for 10 minutes. The column retentate was collected. Protein concentration of lysate was determined and 30 μg was electrophoresed on preparatory SDS-PAGE for Western blot analysis. Strips of 3 mm were cut and probed with the six antibodies and the signal was detected by chemiluminescence.

Figure 3:
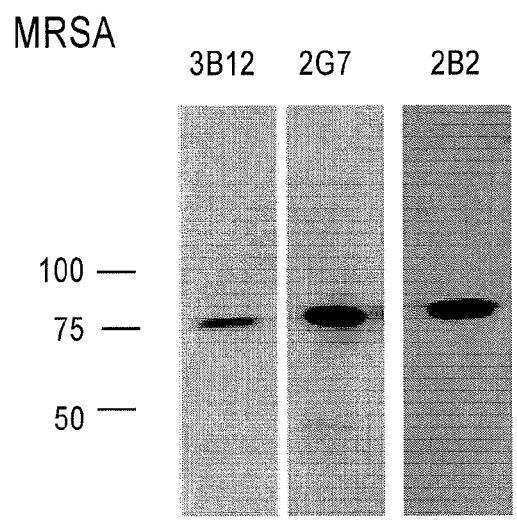
FIG. 3 is a Western analysis of methicillin resistant *Staphylococcus aureus* (MRSA) and methicillin sensitive *Staphylococcus aureus* (MSSA) lysates with antibodies 3B12, 2G7 and 2B2.
Figure 3:
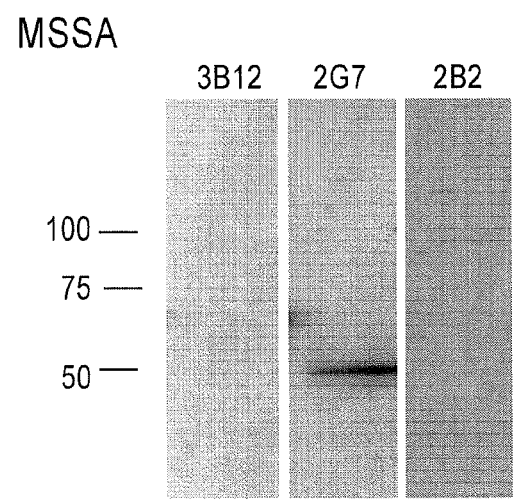

As shown in FIG. 3, all of the three antibodies 3B12, 2G7, 2B2 interacted with a 75 kD polypeptide by Western analysis with the MRSA lysates. With the methicillin sensitive *Staphylococcus aureus* (MSSA) lysates 2G7, interacted with a few peptides of <50 kD. These results indicated that the antibodies had high specificity along with the high sensitivity determined by BIACore analysis. The molecular weight markers in kD are shown on the left.

Example 5

B Cell Generation

The three hybridomas recognizing unique epitopes were isotyped (2G7 (IgG2b) 2B2 (IgG1) and 3B12 (IgG1)) and total RNA was isolated using commercially available kits. First strand cDNA synthesis using random decamers was followed by PCR amplification of the variable light (VL) and variable heavy (VH) regions using isotype-specific primer pairs. The resulting product was cloned into an intermediate vector for sequence analysis. The sequence-verified VL and VH regions were reamplified and the VH region was fused to a defined constant region (CM) by overlap PCR using primer pairs containing specific restriction sites for cloning into the final vectors (pVKExpressGB(puro) for the VL region and pDisplayCuM(hygro) for the VH region) for the 2G7 and 3B12 hybridomas. The corresponding VL and VH containing plasmids were linearized using a unique restriction site and five micrograms of each plasmid was cotransfected by electroporation into the C604 mouse lymphocyte parental B-cell line. The cells were allowed to recover for 24 hours then selected for the presence of the plasmids using the appropriate antibiotics. Approximately two weeks post-transfection surviving pools of cells were primed for 20 hours at 37° C. at 5% $CO_2$ using 2% DMSO in growth media plus antibiotics. The cells were pelleted and resuspended in 50 uM coelentrazine in assay buffer for two hours at 25° C. in the dark. The cells were washed twice in assay buffer followed by an 18 hour incubation in assay buffer at 25° C. in the dark. Pools were normalized to 10,000 cells per assay and screened in duplicate using 60 nanograms recombinant PBP2a conjugated to carboxylated beads (rPBP2a), in assay buffer. Pools exhibiting the highest response to rPBP2a and lowest response to 60 nanograms recombinant protein A-conjugated beads (rPA) by the CANARY® (Innovative Biosensors, Inc., Rockville, Md.) assay were replated in limited dilutions to create clonal colonies. Two weeks post-plating individual clones were screened as described above and scored for their response to rPBP2a and rPA.

Figure 4:
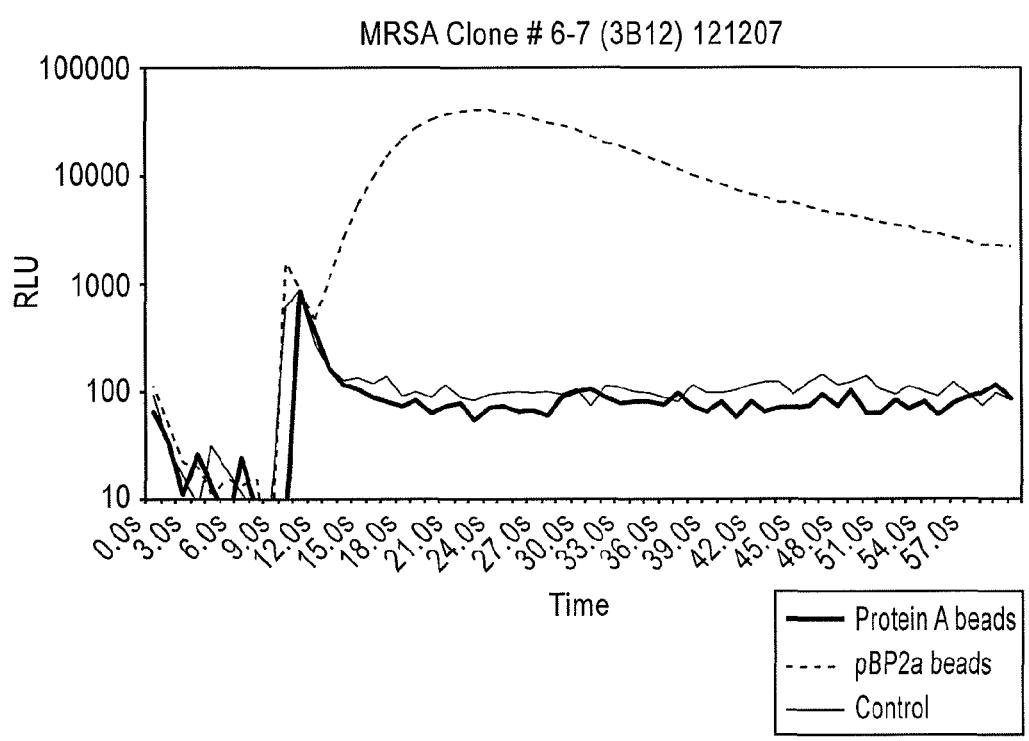
FIG. 4 shows data from a CANARY® assay (Innovative Biosensors, Inc., Rockville, Md.) using antibody 3B12 with recombinant penicillin binding protein 2a (PBP2a) and recombinant protein A (target).
Figure 5:
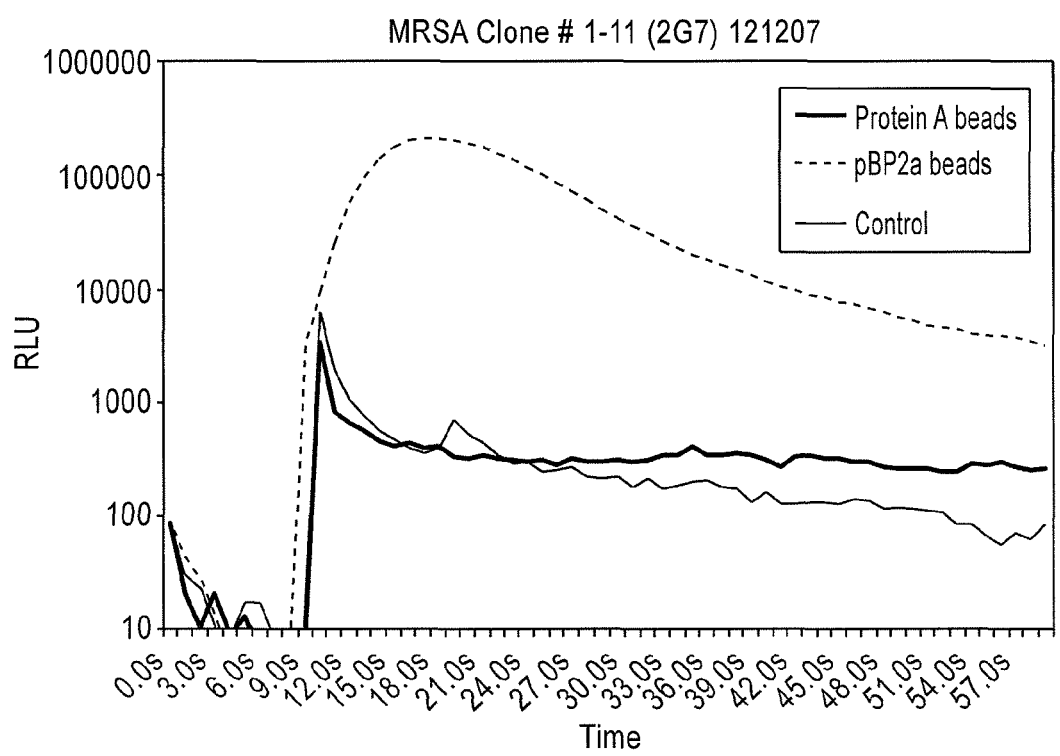
FIG. 5 shows data from a CANARY® assay (Innovative Biosensors, Inc., Rockville, Md.) using antibody 2G7 with recombinant penicillin binding protein 2a (PBP2a) and recombinant protein A.

As shown in FIGS. 4 and 5, robust signals were seen for Clones 3B12 6-7 (FIG. 3) and 2G7 1-11 (FIG. 4) with rPBP2a coupled to carboxylated beads. As shown below the signal for protein A coupled carboxylated beads was minimal. The reaction was measured over a period of 60 seconds.

For a representative clone 2G7 1-4 clone a serial dilution testing of the PBP2a coupled to carboxylated beads was carried out. A signal was observed to a dilution of up to 60 pg as shown in FIG. 6.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular modification of a method of detecting a methicillin resistant S. aureus or is disclosed and discussed and a number of modifications that can be made to the method of detecting a methicillin resistant S. aureus are discussed, each and every combination and permutation of the S. aurues and the detection method are specifically contemplated unless specifically indicated to the contrary. Likewise, any subset or combination of these is also specifically contemplated and disclosed.

Any patents or publications mentioned in the specification are indicative of the level of those skilled in the art. These patents and publications are herein incorporated by reference in their entirety to the same extent as if each individual publication was specifically and individually indicated to be incorporated by reference.

The invention claimed is:

1. A monoclonal antibody selective for PBP2a, or antigen binding fragment thereof, wherein the monoclonal antibody has a binding affinity for PBP2a corresponding to a Kd of at least about $1 \times 10^{-9}$ M, and wherein the monoclonal antibody has the set of light chain complementarity determining regions (CDRs) of SEQ ID NO:4 and the set of heavy chain complementarity determining regions (CDRs) of SEQ ID NO:5.

2. The antibody or antibody fragment of claim 1, wherein the antibody is selective for PBP2a over other antigens present on *Staphylococcus aureas*.

3. The antibody or antibody fragment of claim 2, wherein the antibody does not bind Protein A.

4. The antibody or antibody fragment of claim 1 having a heavy and light chain, wherein the light chain comprises the amino acid sequence of SEQ ID NO:4, and the heavy chain comprises the amino acid sequence of SEQ ID NO:5.

5. The antibody or antibody fragment of claim 1, wherein the antibody is an antibody fragment selected from Fab, Fab', Fab'-SH, scFv, and Fv.

6. The antibody of claim 1, wherein the antibody is a monoclonal antibody expressed on the surface of a cell.

7. The antibody or antibody fragment of claim 1, wherein the antibody has a detectable label.

8. A kit comprising the antibody or antibody fragment of claim 1 and a second antibody against Protein A.

9. The kit of claim 8, wherein at least one antibody is detectably labeled.

10. The kit of claim 8, further comprising reagents for detection.

11. A monoclonal antibody selective for PBP2a, wherein the monoclonal antibody has the set of light chain complementarity determining regions (CDRs) of SEQ ID NO:4 and the set of heavy chain complementarity determining regions (CDRs) of SEQ ID NO:5, and is expressed on the surface of a cell that emits a detectable signal upon binding of the antibody to PBP2a and elevation of intracellular calcium.

12. A method for detecting PBP2a in a sample, comprising, contacting the sample with an antibody or antibody fragment of claim 1 to form a binding complex between PBP2a in the sample and the antibody, and detecting the presence or absence of the binding complex, wherein the presence of the binding complex indicates the presence of PBP2a.

13. The method of claim 12, wherein the sample is suspected of containing methicillin-resistant *Staphylococcus aureus* (MRSA).

14. The method of claim 12 or 13, wherein the sample is from a patient.

15. The method of claim 12 or 13, wherein the sample is from an environmental site.

16. The method of claim 14, wherein the sample is a body fluid.

17. The method of claim 14, wherein the sample is infected.

18. The method of claim 14, wherein the sample is blood, serum, wound drain, sputum, pus, a tissue scraping, washing, or urine.

19. The method of claim 14, wherein the sample is derived from a wound, burn, or ulcer by drainage, irrigation, or swab.

20. The method of claim 12, where antibody binding is detected by a color signal, luminescence, or fluorescence.

21. The method of claim 12, further comprising, capturing, immobilizing or isolating Protein A-containing bacteria.

22. The method of claim 21, wherein the presence of the binding complex on captured, immobilized, or isolated bacteria is indicative of the presence of MRSA.

23. The method of claim 12, wherein the method is an ELISA.

24. The method of claim 21, wherein an antibody against protein A is immobilized, and the antibody against PBP2a is detectably labeled.

25. The method of claim 24, wherein the antibody against PBP2a is immobilized, and the antibody against Protein A is detectably labeled.

26. The method of claim 12, wherein the method is a lateral flow assay.

27. The method of claim 21, wherein an antibody against protein A is immobilized on a chromatographic medium, and the antibody against PBP2a is detectably labeled.

28. The method of claim 26, wherein the antibody against PBP2a is immobilized on a chromatographic medium, and an antibody against Protein A is detectably labeled.

29. The method of claim 12, wherein the sample is treated to lyse bacterial cells.

30. The method of claim 12, wherein the sample is pretreated to isolate or capture intact *Staphylococcus aureus* or lysed *Staphylococcus aureus* cell material.

31. The method of claim 30, wherein the *Staphylococcus aureus* are isolated by antibodies against Protein A.

32. The method of claim 12, wherein the method is performed with a biosensor system employing a sensor cell.

33. The method of claim 32, wherein the sensor cell expresses membrane bound PBP2a-specific antibodies, and a calcium sensitive bioluminescent or fluorescent molecule, wherein binding of the antibodies by PBP2a antigen leads to elevation of intracellular calcium and light emission.

34. The method of claim 33, wherein the amplified light output is detected using a luminometer or optical detector.

35. The method of claim 33 or 34, wherein the sensor cell is a B cell expressing surface bound anti-PBP2a antibodies.

* * * * *